(12) United States Patent
Facchetti et al.

(10) Patent No.: US 8,513,445 B2
(45) Date of Patent: Aug. 20, 2013

(54) POLYCYCLIC AROMATIC MOLECULAR SEMICONDUCTORS AND RELATED COMPOSITIONS AND DEVICES

(75) Inventors: Antonio Facchetti, Chicago, IL (US); Jordan Quinn, Skokie, IL (US); Yu Xia, Skokie, IL (US)

(73) Assignee: Polyera Corporation, Skokie, IL (US)

( * ) Notice: Subject to any disclaimer, the term of this patent is extended or adjusted under 35 U.S.C. 154(b) by 0 days.

(21) Appl. No.: 13/247,559

(22) Filed: Sep. 28, 2011

(65) Prior Publication Data

US 2012/0074394 A1    Mar. 29, 2012

Related U.S. Application Data

(60) Provisional application No. 61/387,643, filed on Sep. 29, 2010.

(51) Int. Cl.
*C07C 50/36* (2006.01)
*H01L 29/08* (2006.01)

(52) U.S. Cl.
USPC .............................. 552/276; 257/40; 552/279

(58) Field of Classification Search
USPC ............................................ 552/276; 257/40
See application file for complete search history.

(56) References Cited

U.S. PATENT DOCUMENTS

| 3,819,664 | A | 6/1974 | Burleigh | 260/356 |
|---|---|---|---|---|
| 4,486,587 | A | 12/1984 | Seybold | 544/99 |
| 4,554,238 | A | 11/1985 | Bushman | 430/258 |
| 6,215,008 | B1 | 4/2001 | Heffron | 552/276 |
| 7,595,093 | B2 | 9/2009 | Ohno et al. | 427/384 |

FOREIGN PATENT DOCUMENTS

| WO | 2004/046082 | 6/2004 |
|---|---|---|
| WO | 2009/130991 | 10/2009 |
| WO | 2010/099583 | 9/2010 |

*Primary Examiner* — Johann R Richter
*Assistant Examiner* — Kofi Adzamli
(74) *Attorney, Agent, or Firm* — Karen K. Chan

(57) ABSTRACT

Disclosed are new semiconductor materials prepared from polycyclic aromatic compounds. Such compounds can exhibit high carrier mobility and/or good current modulation characteristics. In addition, the compounds of the present teachings can possess certain processing advantages such as solution-processability and/or good stability at ambient conditions.

20 Claims, 4 Drawing Sheets

POLYCYCLIC AROMATIC MOLECULAR SEMICONDUCTORS AND RELATED COMPOSITIONS AND DEVICES

REFERENCE TO RELATED APPLICATIONS

This application claims priority to and the benefit of U.S. Provisional Application No. 61/387,643, filed on Sep. 29, 2010, the entire contents of which are incorporated by reference herein.

BACKGROUND

Optoelectronic devices based on organic semiconductors such as organic thin film transistors (OTFTs), organic light-emitting diodes (OLEDs), printable circuits, organic photovoltaic devices, capacitors and sensors are of interest in numerous new technological fields. High speed performance and efficient device operation are necessary for integration of organic materials into commercially-viable products. To achieve this goal, it is desirable that both the hole-transporting (p-type) and electron-transporting (n-type) semiconductor materials in these organic semiconductor-based devices exhibit high charge carrier mobility (μ) and stability under ambient conditions, and can be processed in a cost-effective manner via, for instance, spin-coating or printing methodologies.

Accordingly, the art continues to desire new organic semiconductor materials, particularly those having good stability, processing properties, and/or charge transport characteristics in ambient conditions.

SUMMARY

In light of the foregoing, the present teachings provide organic semiconductors based on polycyclic aromatic compounds that can exhibit properties such as good charge transport characteristics and chemical stability under ambient conditions, low-temperature processability, large solubility in common solvents, and processing versatility. As a result, field effect devices such as thin film transistors that incorporate the present compounds as the semiconductor layer can have high performance under ambient conditions, for example, demonstrating one or more of large electron mobilities, low threshold voltages, and high current on-off ratios.

In various embodiments, the present teachings provide compounds of formula IA and IB:

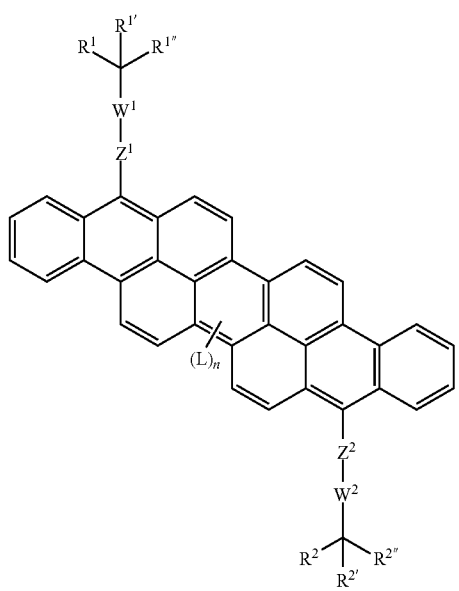

(IA)

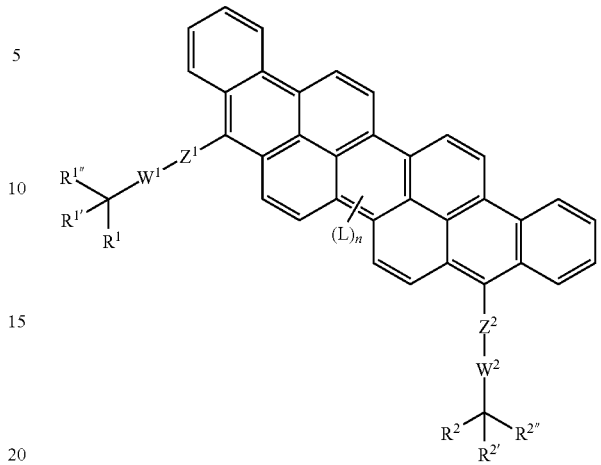

(IB)

wherein L, $W^1$, $W^2$, $Z^1$, $Z^2$, $R^1$, $R^{1'}$, $R^{1''}$, $R^2$, $R^{2'}$, $R^{2''}$, and n are as defined herein.

The present teachings also provide methods of preparing semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF THE DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
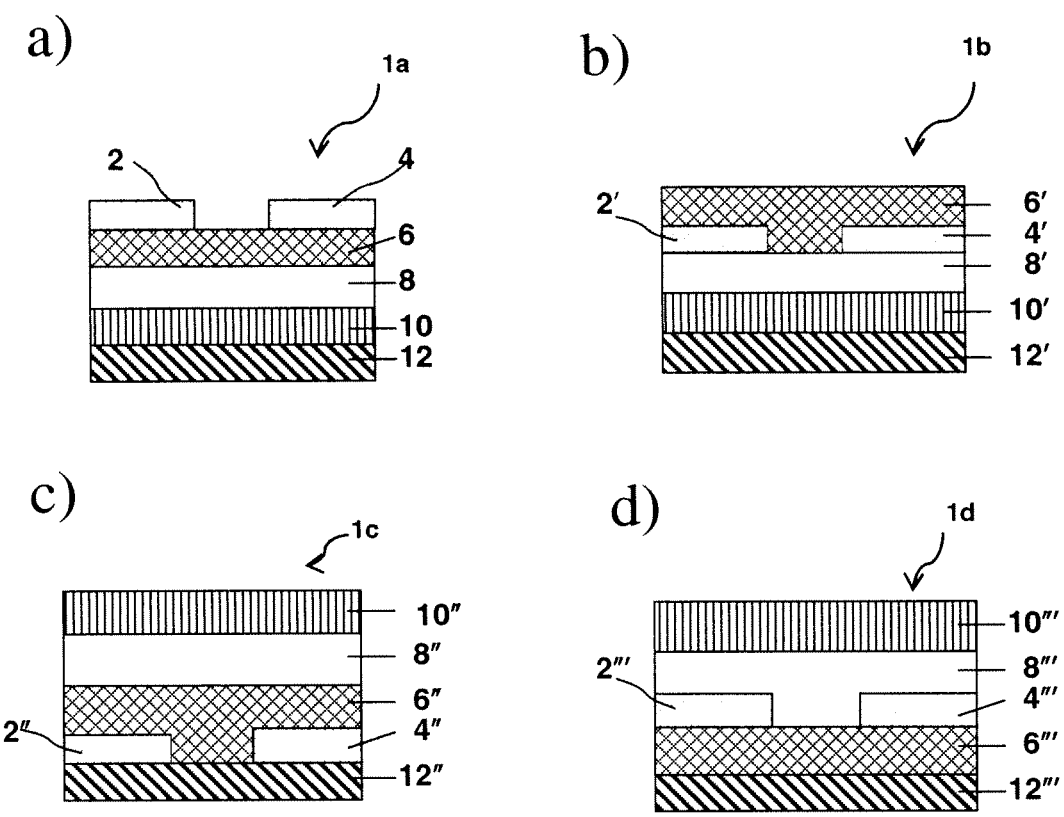
FIG. 1 illustrates four different configurations of thin film transistors: bottom-gate top contact (top left), bottom-gate bottom-contact (top right), top-gate bottom-contact (bottom left), and top-gate top-contact (bottom right); each of which can be used to incorporate polymers of the present teachings.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $—C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein.

As used herein, "alkylthio" refers to an —S-alkyl group (which, in some cases, can be expressed as $—S(O)_w$-alkyl, wherein w is 0). Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and can be optionally substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which can be optionally substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a $—Y—C_{6-14}$ aryl group, where Y is defined as a divalent alkyl group that can be optionally substituted as described herein. An example of an arylalkyl group is a benzyl group ($—CH_2—C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

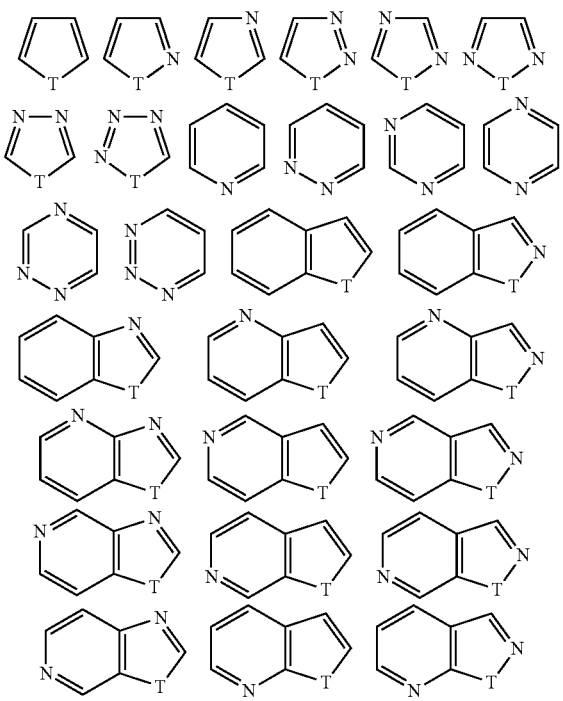

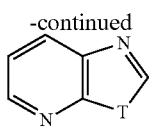

where T is O, S, NH, N-alkyl, N-aryl, N-(arylalkyl) (e.g., N-benzyl), SiH$_2$, SiH-(alkyl), Si(alkyl)$_2$, SiH-(arylalkyl), Si-(arylalkyl)$_2$, or Si(alkyl)(arylalkyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

Compounds of the present teachings can include a "divalent group" defined herein as a linking group capable of forming a covalent bond with two other moieties. For example, compounds of the present teachings can include a divalent C$_{1-20}$ alkyl group (e.g., a methylene group), a divalent C$_{2-20}$ alkenyl group (e.g., a vinylyl group), a divalent C$_{2-20}$ alkynyl group (e.g., an ethynylyl group), a divalent C$_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group." In particular, an "electron-withdrawing group" ("EWG") or an "electron-accepting group" or an "electron-acceptor" refers to a functional group that draws electrons to itself more than a hydrogen atom would if it occupied the same position in a molecule.

Examples of electron-withdrawing groups include, but are not limited to, halogen or halo (e.g., F, Cl, Br, I), —NO$_2$, —CN, —NC, —S(R$^o$)$_2{}^+$, —N(R$^o$)$_3{}^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, C$_{1-40}$ haloalkyl groups, C$_{6-14}$ aryl groups, and 5-14 membered electron-poor heteroaryl groups; where R$^o$ is a C$_{1-40}$ alkyl group, a C$_{2-40}$ alkenyl group, a C$_{2-40}$ alkynyl group, a C$_{1-40}$ haloalkyl group, a C$_{1-40}$ alkoxy group, a C$_{6-14}$ aryl group, a C$_{3-14}$ cycloalkyl group, a 3-14 membered cycloheteroalkyl group, and a 5-14 membered heteroaryl group, each of which can be optionally substituted as described herein.

It should be understood that the term "electron-donating group" can be used synonymously herein with "electron donor." In particular, an "electron-donating group" or an "electron-donor" refers to a functional group that donates electrons to a neighboring atom more than a hydrogen atom would if it occupied the same position in a molecule. Examples of electron-donating groups include —OH, —OR$^o$, —NH$_2$, —NHR$^o$, —N(R$^o$)$_2$, 5-14 membered electron-rich heteroaryl groups, C$_{1-40}$ alkyl groups, C$_{2-40}$ alkenyl groups, C$_{2-40}$ alkynyl groups, C$_{1-40}$ alkoxy groups, where R$^o$ is a C$_{1-40}$ alkyl group, a C$_{2-40}$ alkenyl group, a C$_{2-40}$ alkynyl group, a C$_{6-14}$ aryl group, or a C$_{3-14}$ cycloalkyl group.

At various places in the present specification, substituents are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

As used herein, a "p-type semiconductor material" or a "p-type semiconductor" refers to a semiconductor material having holes as the majority current carriers. In some embodiments, when a p-type semiconductor material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, an "n-type semiconductor material" or an "n-type semiconductor" refers to a semiconductor material having electrons as the majority current carriers. In some embodiments, when an n-type semiconductor material is deposited on a substrate, it can provide an electron mobility in excess of about $10^{-5}$ cm$^2$/Vs. In the case of field-effect devices, an n-type semiconductor can also exhibit a current on/off ratio of greater than about 10.

As used herein, "mobility" refers to a measure of the velocity with which charge carriers, for example, holes (or units of positive charge) in the case of a p-type semiconductor material and electrons in the case of an n-type semiconductor material, move through the material under the influence of an electric field. This parameter, which depends on the device architecture, can be measured using a field-effect device or space-charge limited current measurements.

Throughout the specification, structures may or may not be presented with chemical names. Where any question arises as to nomenclature, the structure prevails.

The present teachings provide various semiconducting small molecule compounds as well as compositions and organic semiconductor materials prepared from such compounds and compositions. The organic semiconductor materials disclosed herein can exhibit useful electrical properties and can be solution-processable, e.g., spin-coatable and printable. In various embodiments, these materials can be considered p-type semiconductors. The semiconductor materials disclosed herein can be used to fabricate various organic electronic articles, structures and devices, including field-effect transistors, unipolar circuitries, complementary circuitries, and photovoltaic devices.

More specifically, the present teachings relate to compounds having formula IA or IB:

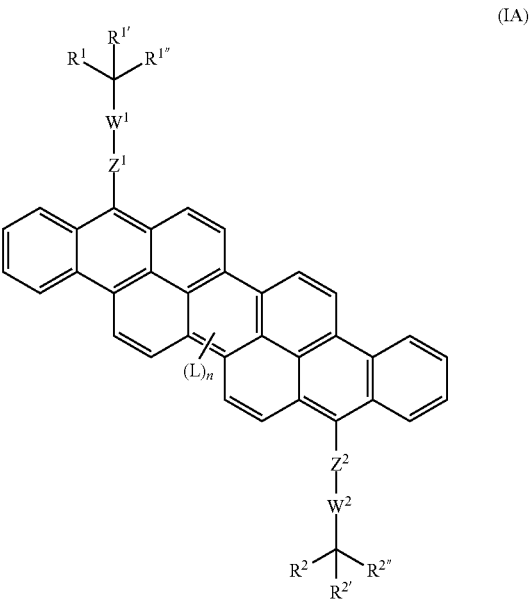

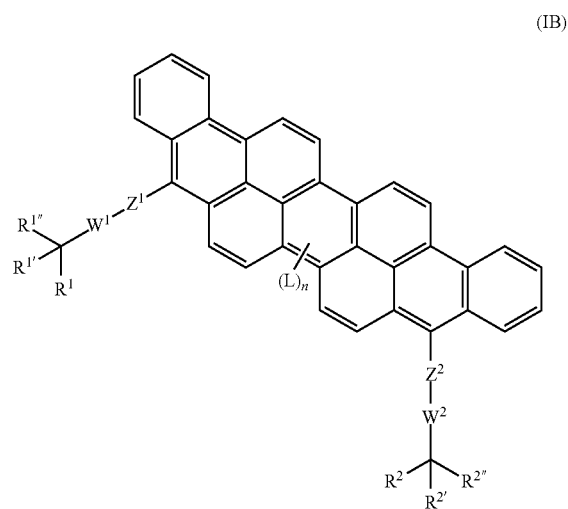

wherein:

$W^1$ and $W^2$ independently can be selected from —$(CR^aR^b)_m$— and —$(SiR^cR^d)$—;

$Z^1$ and $Z^2$ independently can be selected from O, S, —C≡C—, and a covalent bond;

L, at each occurrence, independently can be an electron-withdrawing group;

$R^a$ and $R^b$, at each occurrence, independently can be selected from H, a $C_{1-20}$ alkyl group, and a $C_{1-20}$ haloalkyl group;

$R^c$ and $R^d$ independently can be selected from H, a $C_{1-20}$ alkyl group, and a $C_{1-20}$ haloalkyl group;

$R^1$, $R^{1'}$, $R^{1''}$, $R^2$, $R^{2'}$, and $R^{2''}$ independently can be selected from H, a $C_{1-20}$ alkyl group, a $C_{2-20}$ alkenyl group, and a $C_{1-20}$ haloalkyl group;

m, at each occurrence, independently can be selected from 0, 1, 2, 3, 4, 5, 6, 7, 8, 9, and 10; and n can be selected from 0, 1, 2, 3, 4, 5, 6, 7 and 8.

In various embodiments, $W^1$ and $W^2$ independently can be —$(CR^aR^b)_m$—, where $R^a$, $R^b$, and m are as defined herein. According to these embodiments, each of the groups —$Z^1$—$W^1$—$CR^1R^{1'}R^{1''}$ and —$Z^2$—$W^2$—$CR^2R^{2'}R^{2''}$ can comprise a branched (or non-linear) organic group. For example, each of the groups —$CR^1R^{1'}R^{1''}$ and —$CR^2R^{2'}R^{2''}$ can comprise a branched organic group, when at least two of $R^1$, $R^{1'}$, and $R^{1''}$ and at least two of $R^2$, $R^{2'}$, and $R^{2''}$ are selected from a $C_{1-20}$ alkyl group, a $C_{2-20}$ alkenyl group, and a $C_{1-20}$ haloalkyl group. In addition or alternatively, $W^1$ and $W^2$ can be —$(CR^aR^b)_{1-10}$—, where at least one of $R^a$ and $R^b$ is selected from a $C_{1-20}$ alkyl group and a $C_{1-20}$ haloalkyl group; such that respectively, the groups —$W^1$—$CR^1R^{1'}R^{1''}$ (or —$(CR^aR^b)_m$—$CR^1R^{1'}R^{1''}$) and —$W^2$—$CR^2R^{2'}R^{2''}$ (or —$(CR^aR^b)_m$—$CR^2R^{2'}R^{2''}$) can be selected from a branched $C_{3-40}$ alkyl group, a branched $C_{4-40}$ alkenyl group, and a branched $C_{3-40}$ haloalkyl group. Examples of branched $C_{3-40}$ alkyl groups, branched $C_{4-40}$ alkenyl groups, and branched $C_{3-40}$ haloalkyl groups include:

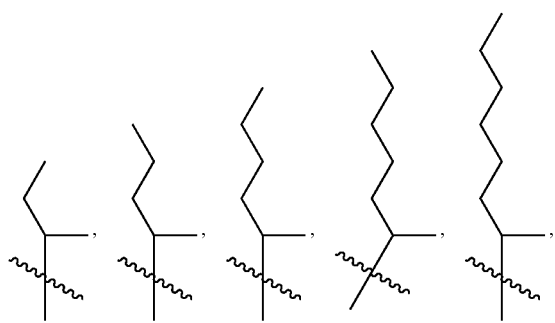

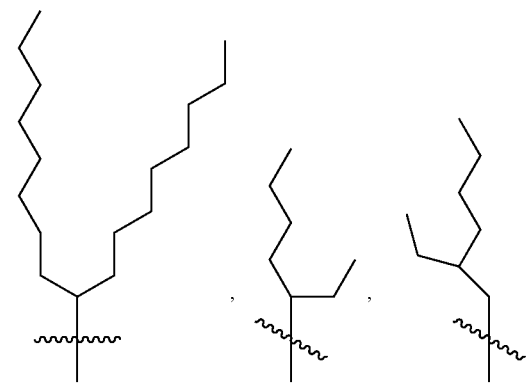

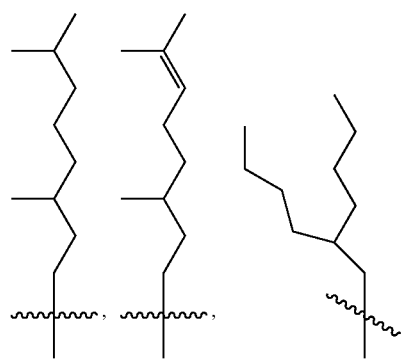

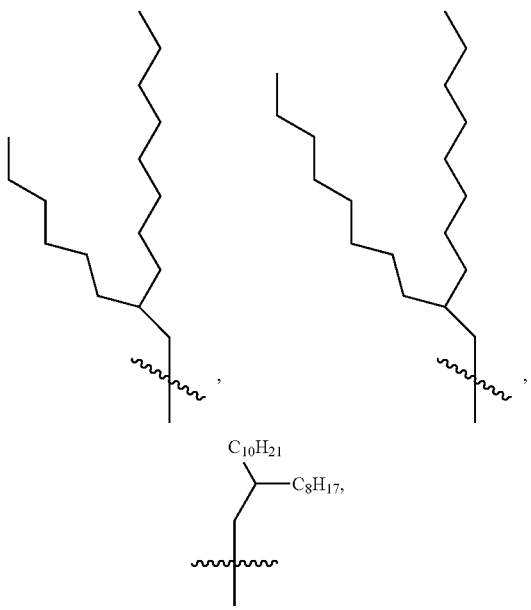

and halo-substituted counterparts thereof.

Accordingly, in these embodiments, the groups —$Z^1$—$W^1$—$CR^1R^{1'}R^{1''}$ and —$Z^2$—$W^2$—$CR^2R^{2'}R^{2''}$, for example, can be selected from a branched $C_{3-40}$ alkoxy group (where $Z^1$ and $Z^2$ are O), a branched $C_{3-40}$ alkylthio group (where $Z^1$ and $Z^2$ are S), and a branched $C_{3-40}$ alkyl, $C_{4-40}$ alkenyl, $C_{5-40}$ alkynyl, or $C_{3-40}$ haloalkyl group (where $Z^1$ and $Z^2$ are —C≡C— or a covalent bond).

In certain embodiments, —$Z^1$—$W^1$—$CR^1R^{1'}R^{1''}$ and —$Z^2$—$W^2$—$CR^2R^{2'}R^{2''}$ can be —$Z^1$—$(CH_2)_m$—$CHR^1R^{1'}$ and —$Z^2$—$(CH_2)_m$—$CHR^2R^{2'}$, respectively, where $R^1$, $R^{1'}$, $R^2$, $R^{2'}$, $Z^1$, $Z^2$, and m are as defined herein. Compounds according to these embodiments can be represented by formula IIA or IIB:

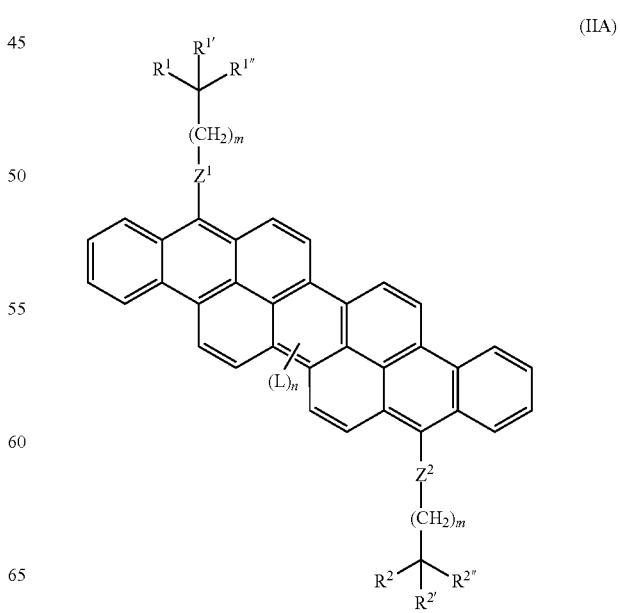

(IIA)

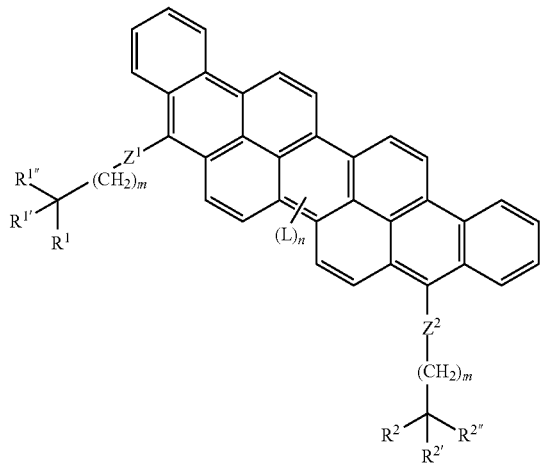

(IIB)

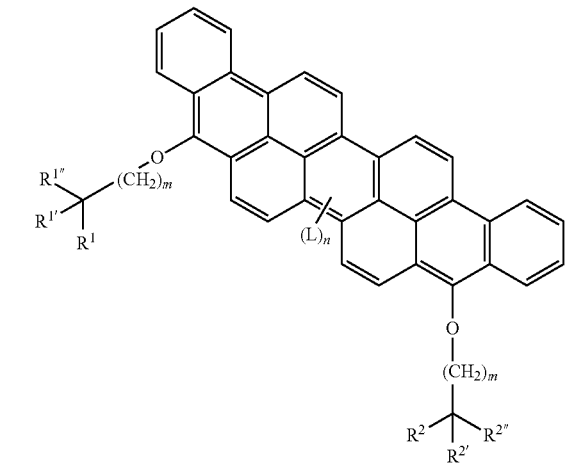

(IIIB)

wherein L, R$^1$, R$^{1'}$, R$^{1''}$, R$^2$, R$^{2'}$, R$^{2''}$, Z$^1$, Z$^2$, m and n are as defined herein. For example, if present, L, at each occurrence, independently can be selected from a halogen (e.g., Br), CN, and NO$_2$; R$^1$, R$^{1'}$, R$^2$, and R$^{2'}$ independently can be selected from a linear C$_{1-20}$ alkyl group, a linear C$_{2-20}$ alkenyl group, and a linear C$_{1-20}$ haloalkyl group; R$^{1''}$ and R$^{2''}$ can be H; Z$^1$ and Z$^2$ independently can be selected from O, S, —C≡C— and a covalent bond; m, at each occurrence, independently can be selected from 0, 1, 2, 3, and 4 (e.g., 0, 1, or 2); and n can be selected from 0, 1, 2, 3, 4, 5, 6, 7, and 8. In certain embodiments, R$^1$ can be different from R$^{1'}$; and R$^2$ can be different from R$^{2'}$. For example, R$^{1'}$ and R$^{2'}$ can be selected from a linear C$_{1-6}$ alkyl group, a linear C$_{2-6}$ alkenyl group, and a linear C$_{1-6}$ haloalkyl group; whereas R$^1$ and R$^2$ can be selected from a linear C$_{3-40}$ alkyl group, a linear C$_{4-40}$ alkenyl group, and a linear C$_{3-40}$ haloalkyl group. In particular embodiments, R$^{1'}$ and R$^{2'}$ can be selected from CH$_3$, CF$_3$, C$_2$H$_5$, CH$_2$CF$_3$, CF$_2$CH$_3$, and C$_2$F$_5$; whereas R$^1$ and R$^2$ can be selected from a linear C$_{3-20}$ alkyl group, a linear C$_{4-20}$ alkenyl group, and a linear C$_{3-20}$ haloalkyl group.

In particular embodiments, —Z$^1$—W$^1$—CR$^1$R$^{1'}$R$^{1''}$ and —Z$^2$—W$^2$—CR$^2$R$^{2'}$R$^{2''}$ can be —O—(CH$_2$)$_m$—CR$^1$R$^{1'}$R$^{1''}$ and —O—(CH$_2$)$_m$—CR$^2$R$^{2'}$R$^{2''}$, respectively, where R$^1$, R$^{1'}$, R$^{1''}$, R$^2$, R$^{2'}$, R$^{2''}$ and m are as defined herein. Compounds according to these embodiments can be represented by formula IIIA or IIIB:

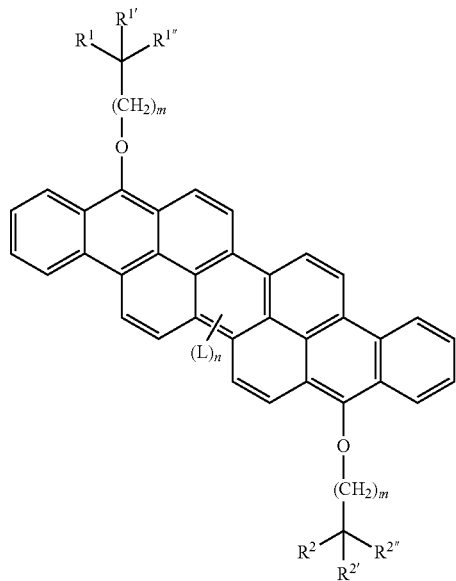

(IIIA)

wherein L, R$^1$, R$^{1'}$, R$^{1''}$, R$^2$, R$^{2'}$, R$^{2''}$, m and n are as defined herein. For example, if present, L, at each occurrence, independently can be selected from a halogen (e.g., Br), CN, and NO$_2$; R$^1$, R$^{1'}$, R$^2$, and R$^{2'}$ independently can be selected from a linear C$_{1-20}$ alkyl group, a linear C$_{2-20}$ alkenyl group, and a linear C$_{1-20}$ haloalkyl group; R$^{1''}$ and R$^{2''}$ can be H; m, at each occurrence, independently can be selected from 0, 1, 2, 3, and 4 (e.g., 0, 1, or 2); and n can be selected from 0, 1, 2, 3, 4, 5, 6, 7, and 8. In certain embodiments, R$^1$ can be different from R$^{1'}$; and R$^2$ can be different from R$^{2'}$. For example, R$^{1'}$ and R$^{2'}$ can be selected from CH$_3$, CF$_3$, C$_2$H$_5$, CH$_2$CF$_3$, CF$_2$CH$_3$, and C$_2$F$_5$; and R$^1$ and R$^2$ can be selected from a linear C$_{3-20}$ alkyl group, a linear C$_{4-20}$ alkenyl group, and a linear C$_{3-20}$ haloalkyl group.

In particular embodiments, —Z$^1$—W$^1$—CR$^1$R$^{1'}$R$^{1''}$ and —Z$^2$—W$^2$—CR$^2$R$^{2'}$R$^{2''}$ can be —C≡C—(CH$_2$)$_m$—CR$^1$R$^{1'}$R$^{1''}$ and —C≡C—(CH$_2$)$_m$—CR$^2$R$^{2'}$R$^{2''}$, respectively, where R$^1$, R$^{1'}$, R$^{1''}$, R$^2$, R$^{2'}$, R$^{2''}$ and m are as defined herein. Compounds according to these embodiments can be represented by formula IVA or IVB:

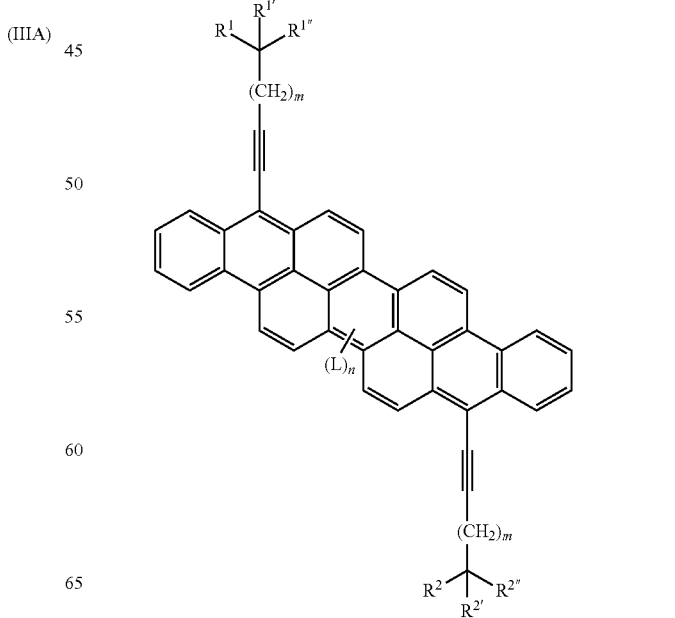

(IVA)

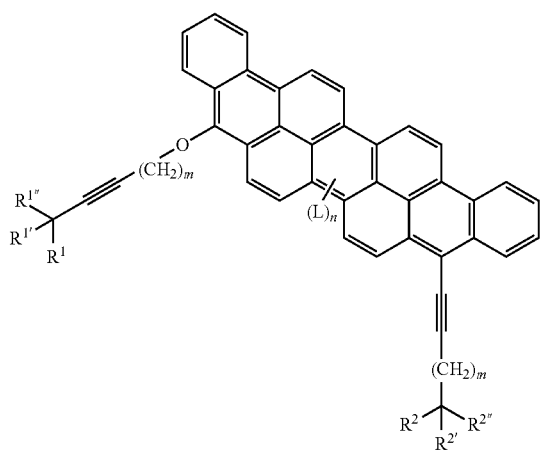

(IVB)

wherein L, R$^1$, R$^{1'}$, R$^{1''}$, R$^2$, R$^{2'}$, R$^{2''}$, m and n are as defined herein. For example, if present, L, at each occurrence, independently can be selected from a halogen (e.g., Br), CN, and NO$_2$; R$^1$, R$^{1'}$, R$^2$, and R$^{2'}$ independently can be selected from a linear C$_{1\text{-}20}$ alkyl group, a linear C$_{2\text{-}20}$ alkenyl group, and a linear C$_{1\text{-}20}$ haloalkyl group; R$^{1''}$ and R$^{2''}$ can be H; m, at each occurrence, independently can be selected from 0, 1, 2, 3, and 4 (e.g., 0, 1, or 2); and n can be selected from 0, 1, 2, 3, 4, 5, 6, 7, and 8. In certain embodiments, R$^1$ can be different from R$^{1'}$; and R$^2$ can be different from R$^{2'}$. For example, R$^{1'}$ and R$^{2'}$ can be selected from CH$_3$, CF$_3$, C$_2$H$_5$, CH$_2$CF$_3$, CF$_2$CH$_3$, and C$_2$F$_5$; and R$^1$ and R$^2$ can be selected from a linear C$_{3\text{-}20}$ alkyl group, a linear C$_{4\text{-}20}$ alkenyl group, and a linear C$_{3\text{-}20}$ haloalkyl group.

In particular embodiments, —Z$^1$—W$^1$—CR$^1$R$^{1'}$R$^{1''}$ and —Z$^2$—W$^2$—CR$^2$R$^{2'}$R$^{2''}$ can be —(CH$_2$)$_m$—CR$^1$R$^{1'}$R$^{1''}$ and —(CH$_2$)$_m$—CR$^2$R$^{2'}$R$^{2''}$, respectively, where R$^1$, R$^{1'}$, R$^{1''}$, R$^2$, R$^{2'}$, R$^{2''}$ and m are as defined herein. Compounds according to these embodiments can be represented by formula VA or VB:

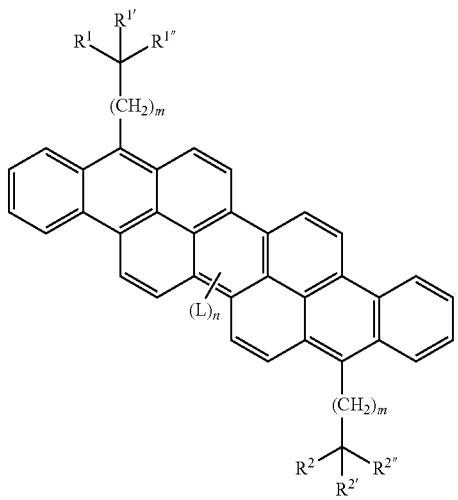

(VA)

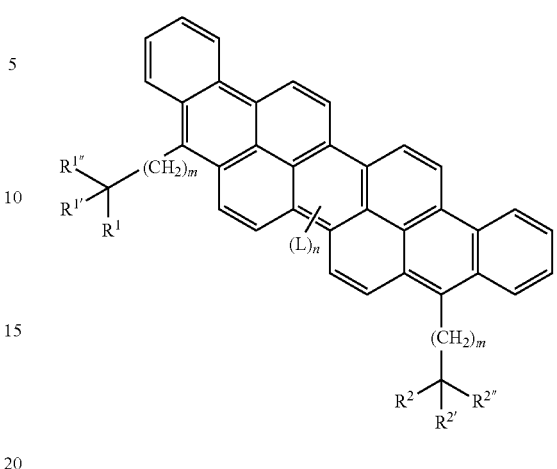

(VB)

wherein L, R$^1$, R$^{1'}$, R$^{1''}$, R$^2$, R$^{2'}$, R$^{2''}$, m and n are as defined herein. For example, if present, L, at each occurrence, independently can be selected from a halogen (e.g., Br), CN, and NO$_2$; R$^1$, R$^{1'}$, R$^2$, and R$^{2'}$ independently can be selected from a linear C$_{1\text{-}20}$ alkyl group, a linear C$_{2\text{-}20}$ alkenyl group, and a linear C$_{1\text{-}20}$ haloalkyl group; R$^{1''}$ and R$^{2''}$ can be H; m, at each occurrence, independently can be selected from 0, 1, 2, 3, and 4 (e.g., 0, 1, or 2); and n can be selected from 0, 1, 2, 3, 4, 5, 6, 7, and 8. In certain embodiments, R$^1$ can be different from R$^{1'}$; and R$^2$ can be different from R$^{2'}$. For example, R$^{1'}$ and R$^{2'}$ can be selected from CH$_3$, CF$_3$, C$_2$H$_5$, CH$_2$CF$_3$, CF$_2$CH$_3$, and C$_2$F$_5$; and R$^1$ and R$^2$ can be selected from a linear C$_{3\text{-}20}$ alkyl group, a linear C$_{4\text{-}20}$ alkenyl group, and a linear C$_{3\text{-}20}$ haloalkyl group.

In various embodiments, L can be present (i.e., n is selected from 1, 2, 3, 4, 5, 6, 7, 8, 9 and 10) and can be selected from a halogen (e.g., F, Cl, or Br), CN, and NO$_2$. In other embodiments, n can be 0. That is, various compounds according to formula IA and IB can have no further substituents other than the groups —Z$^1$—W$^1$—CR$^1$R$^{1'}$R$^{1''}$ and —Z$^2$—W$^2$—CR$^2$R$^{2'}$R$^{2''}$. For example, certain compounds of the present teachings can be presented by formula IIAa:

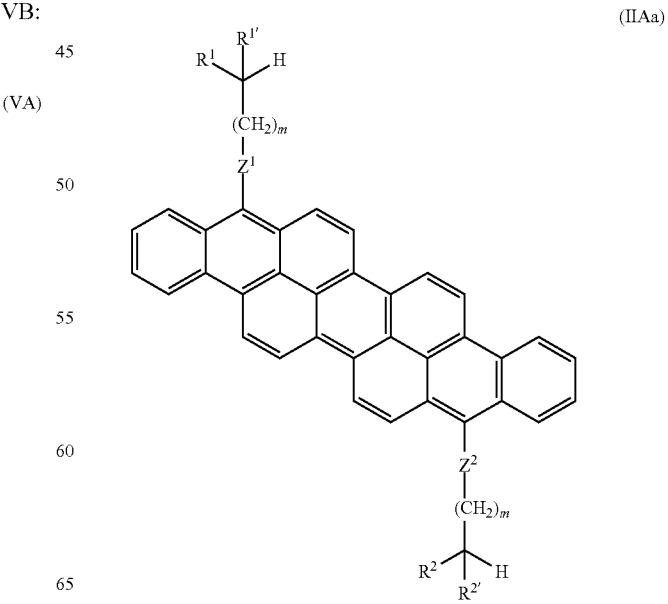

(IIAa)

where $R^1$, $R^{1'}$, $R^2$, $R^{2'}$, $Z^1$, $Z^2$, and m are as defined herein. To illustrate, $Z^1$ and $Z^2$ can be selected from O, —C≡C—, and a covalent bond; and compounds according to these embodiments can be represented by formula IIIAa, IVAa, or VAa:

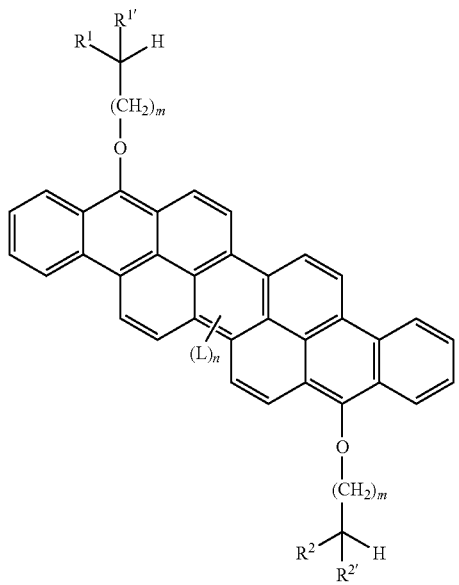
(IIIAa)

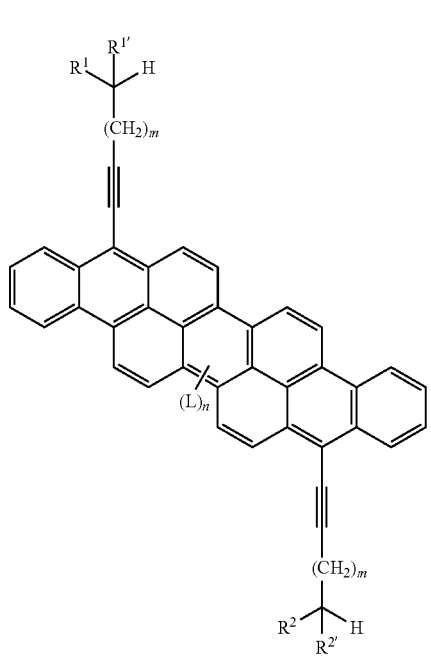
(IVAa)

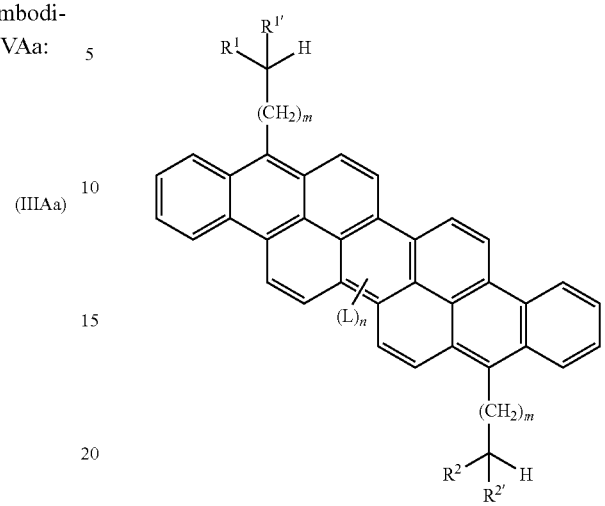
(VAa)

where $R^1$, $R^{1'}$, $R^2$, $R^{2'}$, and m are as defined herein. For example, $R^1$ and $R^2$ independently can be selected from a linear $C_{3-20}$ alkyl group, a linear $C_{4-20}$ alkenyl group, and a linear $C_{3-20}$ haloalkyl group; $R^{1'}$ and $R^{2'}$ independently can be selected from $CH_3$, $CF_3$, $C_2H_5$, $CH_2CF_3$, $CF_2CH_3$, and $C_2F_5$; and each m independently can be selected from 0, 1, and 2.

To further illustrate, various compounds according to the present teachings can have $—Z^1—W^1—CR^1R^{1'}R^{1'''}$ and $—Z^2—W^2—CR^2R^{2'}R^{2''}$ groups where the groups $—W^1—CR^1R^{1'}R^{1'''}$ and $—W^2—CR^2R^{2'}R^{2''}$ can be selected from:

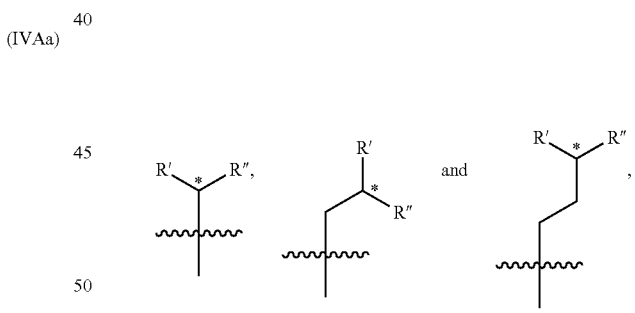

where R' is a $C_{1-20}$ alkyl or haloalkyl group; R" is different from R' and selected from a $C_{1-20}$ alkyl group, a $C_{2-20}$ alkenyl group, and a $C_{1-20}$ haloalkyl group; and $Z^1$ and $Z^2$ are as defined herein. Because R" is different from R', the common carbon atom to which R' and R" are connected is a stereogenic center (as denoted by the asterisk (*)), and accordingly, a compound of formula IA or IB can be optically active (e.g., when $—W^1—CR^1R^{1'}R^{1'''}$ and $—W^2—CR^2R^{2'}R^{2''}$ are compositionally and stereoisomerically identical) or optically inactive (e.g., when —W¹—CR¹R¹'R¹'' and —W²—CR²R²'R²'' are compositionally identical but stereoisomerically different). For example, certain compounds of the present teachings can be presented by formula IIAb or IIAc:

—C≡C—, and a covalent bond; and compounds according to these embodiments can be represented by formula IIIAb, IIIAc, IVAb, IVAc, VAb or VAc:

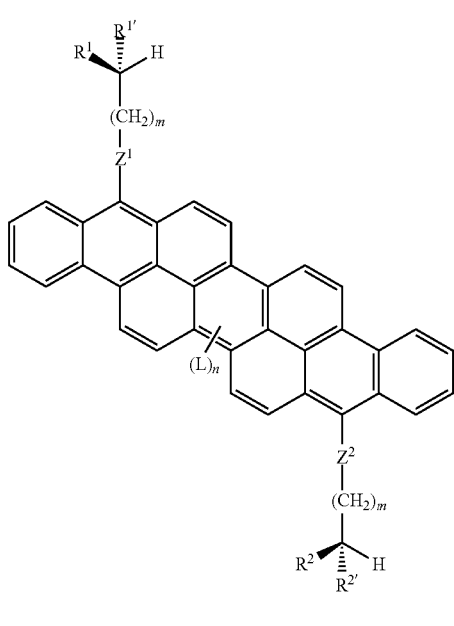
(IIAb)

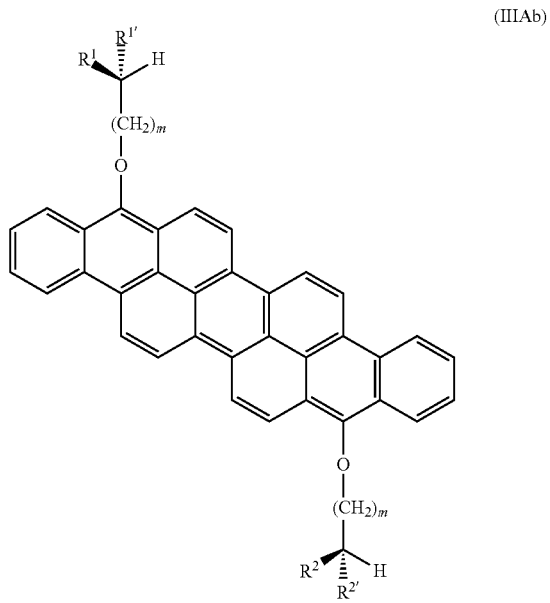
(IIIAb)

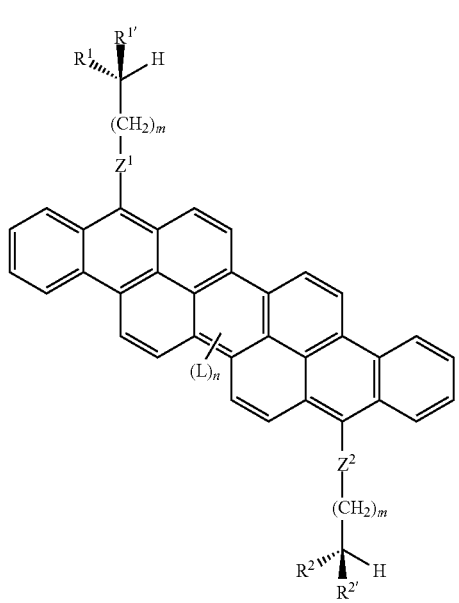
(IIAc)

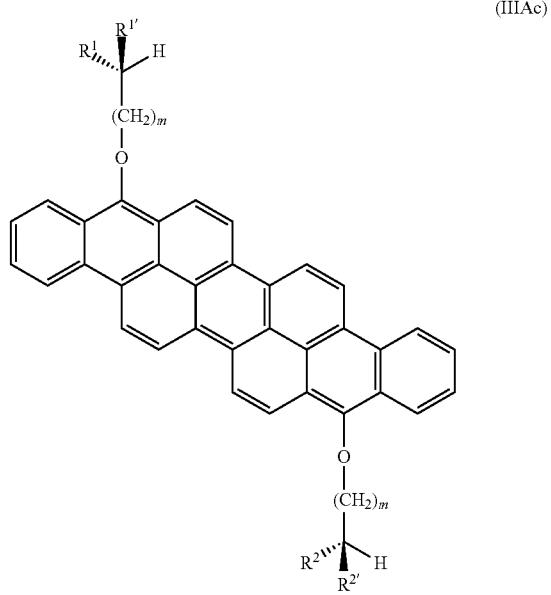
(IIIAc)

where R¹, R¹', R², R²', Z¹, Z², and m are as defined herein. In particular embodiments, Z¹ and Z² can be selected from O, (IVAb)

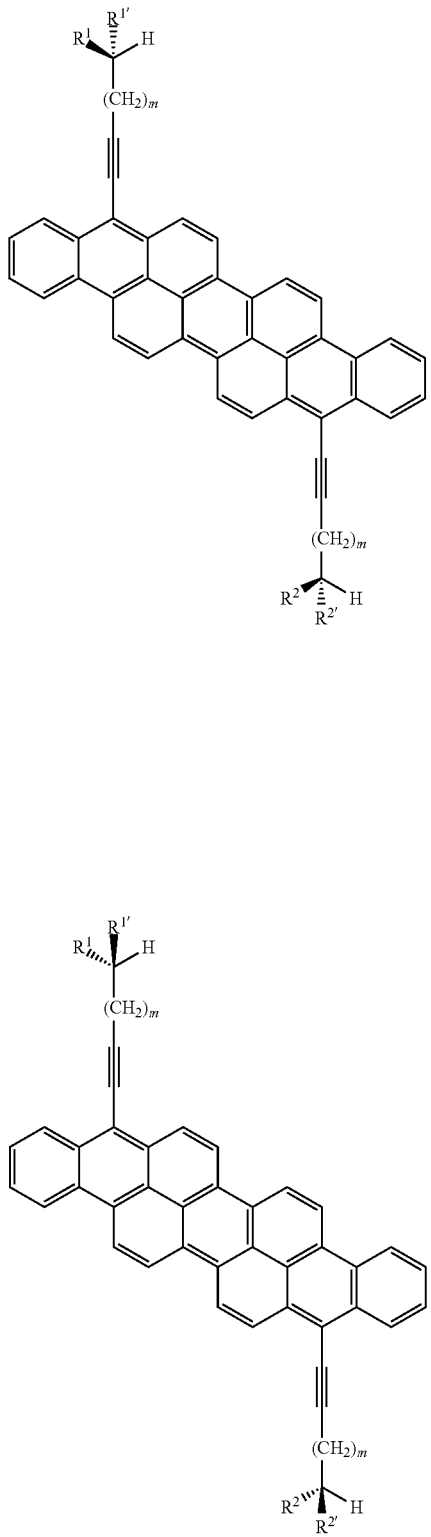

(IVAc)

(VAb)

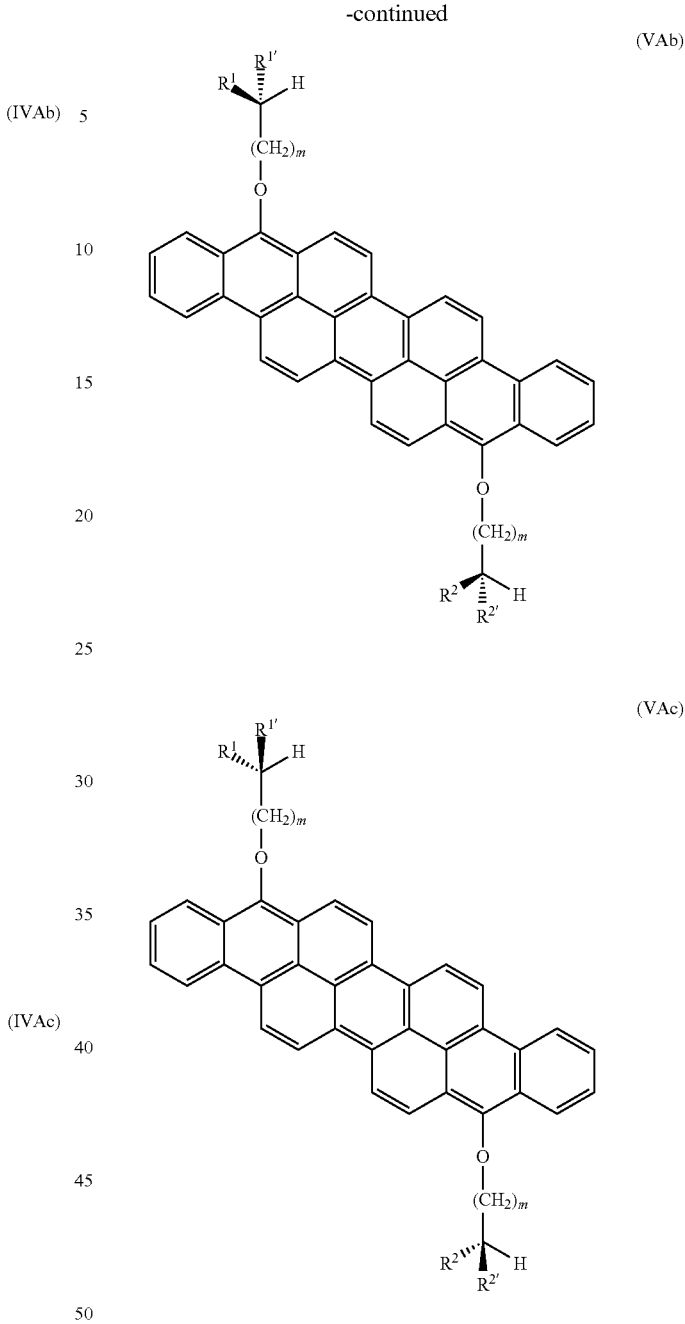

(VAc)

where $R^1$, $R^{1'}$, $R^2$, $R^{2'}$, and m are as defined herein. For example, $R^1$ and $R^2$ independently can be selected from a linear $C_{3-20}$ alkyl group, a linear $C_{4-20}$ alkenyl group, and a linear $C_{3-20}$ haloalkyl group; $R^{1'}$ and $R^{2'}$ independently can be selected from $CH_3$, $CF_3$, $C_2H_5$, $CH_2CF_3$, $CF_2CH_3$, and $C_2F_5$; and each m independently can be selected from 0, 1, and 2.

In some embodiments of compounds of formula IA or IB, $W^1$ and $W^2$ can be —(SiR$^c$R$^d$)—, where $R^c$ and $R^d$ are as defined herein. For example, at least one of $R^c$ and $R^d$ can be selected from a $C_{1-20}$ alkyl group and a $C_{1-20}$ haloalkyl group. In some of these embodiments, $Z^1$ and $Z^2$ can be —C≡C—. Accordingly, certain compounds according to these embodiments can be represented by formula VIA or VIB:

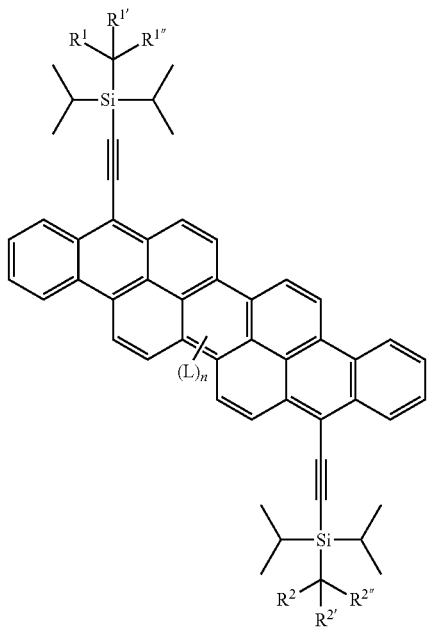

(VIA)

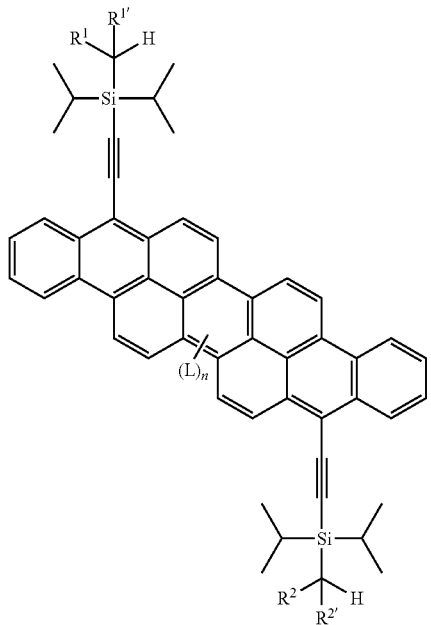

(VIAa)

where $R^1$, $R^{1'}$, $R^2$, and $R^{2'}$ independently can be selected from $CH_3$, $CF_3$, $C_2H_5$, $CH_2CF_3$, $CF_2CH_3$, and $C_2F_5$; L, at each occurrence, independently can be selected from Br, CN, and $NO_2$; and n can be 1, 2, 3, 4, 5, 6, 7 or 8. For example, L can be Br; each of $R^1$, $R^{1'}$, $R^2$, and $R^{2'}$ can be $CH_3$; and n can be 4 or 8.

In particular embodiments, $R^1$ can be the same as $R^2$ but different from $R^{1'}$, and $R^{2'}$ can be the same as $R^{1'}$ but different from $R^2$, such that the common carbon atom to which $R^1$ and $R^{1'}$ are connected and the carbon atom to which the common carbon atom to which $R^2$ and $R^{2'}$ are connected are stereogenic centers. Certain compounds according to these embodiments can be represented by formula VIAb and VIAc:

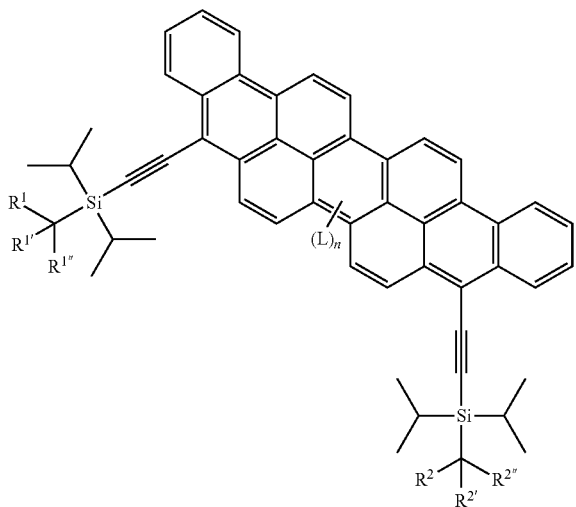

(VIB)

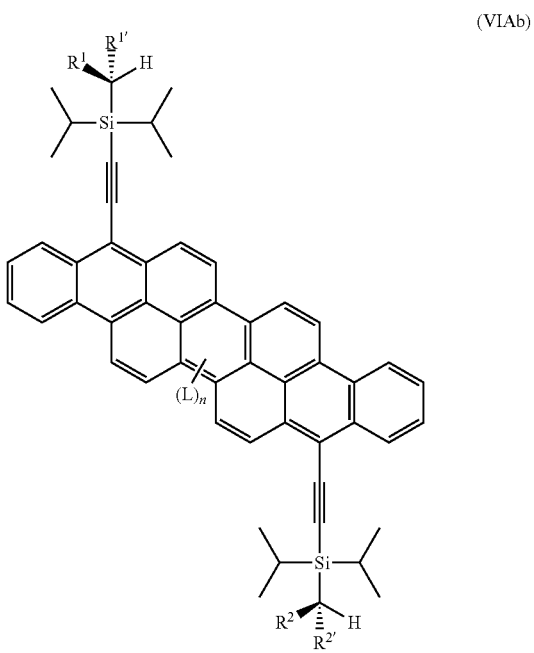

(VIAb)

wherein L, $R^1$, $R^{1'}$, $R^{1''}$, $R^2$, $R^{2'}$, $R^{2''}$ and n are as defined herein. For example, L can be present and selected from a halogen (e.g., Br, Cl, or F), CN, and $NO_2$; and $R^{1''}$ and $R^{2''}$ can be H.

Accordingly, certain compounds according to embodiments where $W^1$ and $W^2$ are —($SiR^cR^d$)— can be represented by formula VIAa:

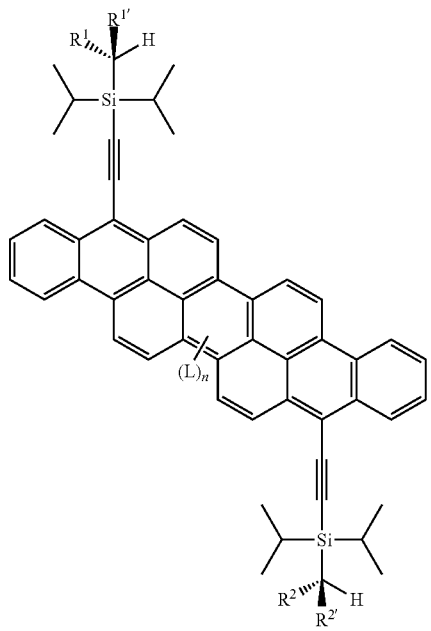

(VIAc)

where $R^1$, $R^{1''}$, $R^2$, and $R^{2'}$ independently can be selected from $CH_3$, $CF_3$, $C_2H_5$, $CH_2CF_3$, $CF_2CH_3$, and $C_2F_5$; L, at each occurrence, independently can be selected from Br, CN, and $NO_2$; and n can be 1, 2, 3, 4, 5, 6, 7 or 8. For example, L can be Br; each of $R^1$, $R^{1'}$, $R^2$, and $R^{2'}$ can be $CH_3$; and n can be 4 or 8.

It should be understood that the present teachings can exclude certain compounds of formula IA and/or IB. For example, the present teachings can exclude certain compounds of formula IA and/or IB where n is 0, and —$Z^1$—$W^1$—$CR^1R^{1'}R^{1''}$ and —$Z^2$—$W^2$—$CR^2R^{2'}R^{2''}$ are —C≡C—Si(isopropyl)$_3$. The present teachings also can exclude certain compounds of formula IA and/or IB where n is 0, $Z^1$ and $Z^2$ are —C≡C—, $W^1$ and $W^2$ are —Si($R^cR^d$)—, and $R^1$, $R^{1'}$, $R^{1''}$, $R^2$, $R^{2'}$, $R^{2''}$, $R^c$ and $R^d$ are selected from H and a $C_{1-20}$ alkyl group.

Compounds of the present teachings can be prepared according to procedures described in Examples 1-6. Alternatively, the present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the polymers described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Various compounds according to the present teachings can have good charge transport properties and can be stable under ambient conditions ("ambient stable"), soluble in common solvents, and in turn solution-processable into various articles, structures, or devices. Accordingly, the present teachings provide for electronic devices, optical devices, and optoelectronic devices that include one or more compounds described herein as semiconductors. Examples of such electronic devices, optical devices, and optoelectronic devices include thin film semiconductors, thin film transistors (e.g., field effect transistors), photovoltaics, photodetectors, organic light-emitting devices such as organic light-emitting diodes (OLEDs) and organic light-emitting transistors (OLETs), complementary metal oxide semiconductors (CMOSs), complementary inverters, diodes, capacitors, sensors, D flip-flops, rectifiers, and ring oscillators. In some embodiments, the present teachings provide for a thin film semiconductor including one or more compounds described herein and a field effect transistor device including the thin film semiconductor. In particular, the field effect transistor device has a structure selected from top-gate bottom-contact structure, bottom-gate top-contact structure, top-gate top-contact structure, and bottom-gate bottom-contact structure. In certain embodiments, the field effect transistor device includes a dielectric material, wherein the dielectric material includes an organic dielectric material, an inorganic dielectric material, or a hybrid organic/inorganic dielectric material. In other embodiments, the present teachings provide for photovoltaic devices and organic light-emitting devices incorporating a thin film semiconductor that includes one or more compounds described herein.

Compounds of the present teachings generally have good solubility in a variety of common solvents. Thus, various embodiments of the present compounds can be processed via inexpensive solution-phase techniques into electronic devices, optical devices, or optoelectronic devices. As used herein, a compound can be considered soluble in a solvent when at least 1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone and methyl ethyl ketone; ethers such as tetrahydrofuran, dioxane, bis(2-methoxyethyl)ether, diethyl ether, diisopropyl ether, and t-butyl methyl ether; alcohols such as methanol, ethanol, butanol, and isopropyl alcohol; aliphatic hydrocarbons such as hexanes; acetates such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. Examples of common inorganic solvents include water and ionic liquids.

Accordingly, the present teachings further provide compositions that include one or more compounds disclosed herein dissolved or dispersed in a liquid medium, for example, an organic solvent, an inorganic solvent, or combinations thereof (e.g., a mixture of organic solvents, inorganic solvents, or organic and inorganic solvents). In some embodiments, the composition can further include one or more additives independently selected from detergents, dispersants, binding agents, compatiblizing agents, curing agents, initiators, humectants, antifoaming agents, wetting agents, pH modifiers, biocides, and bactereriostats. For example, surfactants and/or other polymers (e.g., polystyrene, polyethylene, poly-alpha-methylstyrene, polyisobutene, polypropylene, polymethylmethacrylate, and the like) can be included as a dispersant, a binding agent, a compatiblizing agent, and/or an antifoaming agent.

Various deposition techniques, including various solution-processing techniques, have been used with organic electronics. For example, much of the printed electronics technology has focused on inkjet printing, primarily because this technique offers greater control over feature position and multilayer registration. Inkjet printing is a noncontact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include screen-printing, gravure, offset, flexo, and microcontact printing. Other solution processing techniques include, for example, spin coating, drop-casting, zone casting, dip coating, and blade coating.

The present compounds can exhibit versatility in their processing. Formulations including the present compounds can be printable via different types of printing techniques including gravure printing, flexographic printing, and inkjet printing, providing smooth and uniform films that allow, for example, the formation of a pinhole-free dielectric film thereon, and consequently, the fabrication of all-printed devices.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more compounds disclosed herein. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying. More expensive processes such as vapor deposition also can be used.

The present teachings further provide articles of manufacture, for example, composites that include a thin film semiconductor of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), self-assembled superlattice/self-assembled nanodielectric (SAS/SAND) materials (e.g., as described in Yoon, M-H. et al., *PNAS*, 102 (13): 4678-4682 (2005), the entire disclosure of which is incorporated by reference herein), as well as hybrid organic/inorganic dielectric materials (e.g., as described in U.S. Pat. No. 7,678,463, the entire disclosure of which is incorporated by reference herein). In some embodiments, the dielectric component can include the crosslinked polymer blends described in U.S. Pat. No. 7,605,394, the entire disclosure of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene)poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs) and organic light-emitting transistors (OLETs), as well as sensors, capacitors, unipolar circuits, complementary circuits (e.g., inverter circuits), and the like.

Accordingly, an aspect of the present teachings relates to methods of fabricating an organic thin film transistor that incorporates a semiconductor material of the present teachings. The semiconductor materials of the present teachings can be used to fabricate various types of organic thin film transistors including top-gate top-contact capacitor structures, top-gate bottom-contact capacitor structures, bottom-gate top-contact capacitor structures, and bottom-gate bottom-contact capacitor structures.

FIG. 1 illustrates the four common types of OFET structures: (top left) bottom-gate top-contact structure, (top right) bottom-gate bottom-contact structure, (bottom left) top-gate bottom-contact structure, and (bottom right) top-gate top-contact structure. As shown in FIG. 1, an OFET can include a gate dielectric component (e.g., shown as 8, 8', 8'', and 8'''), a semiconductor component or semiconductor layer (e.g., shown as 6, 6', 6'', and 6'''), a gate electrode or contact (e.g., shown as 10, 10', 10'', and 10'''), a substrate (e.g., shown as 12, 12', 12'', and 12'''), and source and drain electrodes or contacts (e.g., shown as 2, 2', 2'', 2''', 4, 4', 4'', and 4'''). As shown, in each of the configurations, the semiconductor component is in contact with the source and drain electrodes, and the gate dielectric component is in contact with the semiconductor component on one side and the gate electrode on an opposite side. For OLETs, similar architecture can be adopted where the semiconductor layer is replaced with one or more layers that individually or in combination perform the functions of hole transport, electron transport, and emission.

In certain embodiments, OTFT devices can be fabricated with one or more compounds disclosed herein on doped silicon substrates, using $SiO_2$ as the dielectric, in top-contact geometries. In particular embodiments, the active semiconductor layer which incorporates one or more compounds disclosed herein can be deposited at room temperature or at an elevated temperature. In other embodiments, the active semiconductor layer which incorporates one or more compounds disclosed herein can be applied by spin-coating or printing as described herein. For top-contact devices, metallic contacts can be patterned on top of the films using shadow masks.

In certain embodiments, OTFT devices can be fabricated with one or more compounds disclosed herein on plastic foils, using polymers as the dielectric, in top-gate bottom-contact geometries. In particular embodiments, the active semiconducting layer which incorporates one or more compounds disclosed herein can be deposited at room temperature or at an elevated temperature. In other embodiments, the active semiconducting layer which incorporates one or more compounds disclosed herein can be applied by spin-coating or printing as described herein. Gate and source/drain contacts can be made of Au, other metals, or conducting polymers and deposited by vapor-deposition and/or printing.

In various embodiments, a semiconducting component incorporating one or more compounds disclosed herein can exhibit p-type semiconducting activity, for example, a hole mobility of $10^{-4}$ cm$^2$/V-sec or greater (e.g., $10^{-3}$ cm$^2$/V-sec or greater, or $10^{-2}$ cm$^2$/V-sec or greater) and/or a current on/off ratio ($I_{on}/I_{off}$) of $10^3$ or greater (e.g., $10^4$ or greater, or $10^5$ or greater).

Other articles of manufacture in which one or more compounds disclosed herein can be useful include photovoltaics or solar cells. The present compounds can exhibit broad optical absorption and/or tuned redox properties and bulk carrier mobilities. Accordingly, the present compounds can be used, for example, as a p-type semiconductor in a photovoltaic design, which includes an adjacent n-type semiconductor to form a p-n junction. The present compounds can be in the form of a thin film semiconductor, or a composite including the thin film semiconductor deposited on a substrate.

Figure 2:
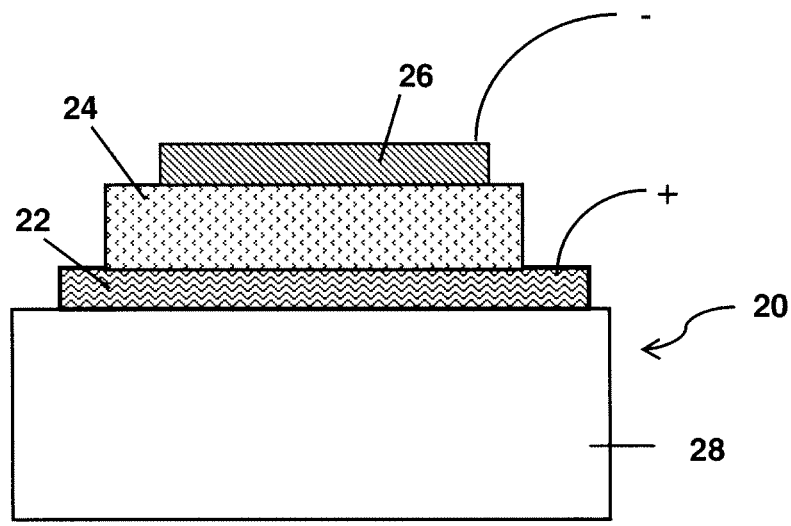
FIG. 2 illustrates a representative structure of a bulk-heterojunction organic photovoltaic device (also known as solar cell) which can incorporate one or more compounds of the present teachings as the donor and/or acceptor materials.

FIG. 2 illustrates a representative structure of a bulk-heterojunction organic photovoltaic device (also known as solar cell) which can incorporate one or more compounds of the present teachings as the donor and/or acceptor materials. As shown, a representative solar cell generally includes a substrate 20 (e.g., glass), an anode 22 (e.g., ITO), a cathode 26 (e.g., aluminium or calcium), and a photoactive layer 24 disposed between the anode and the cathode which can incorporate one or more compounds of the present teachings as the electron donor (p-channel) and/or electron acceptor (n-channel) materials. For example, the photoactive layer 24 can be composed of a blend material that includes one or more compounds according to the present teachings blended with one or more fullerene derivatives (e.g., PCBM).

Figure 3:
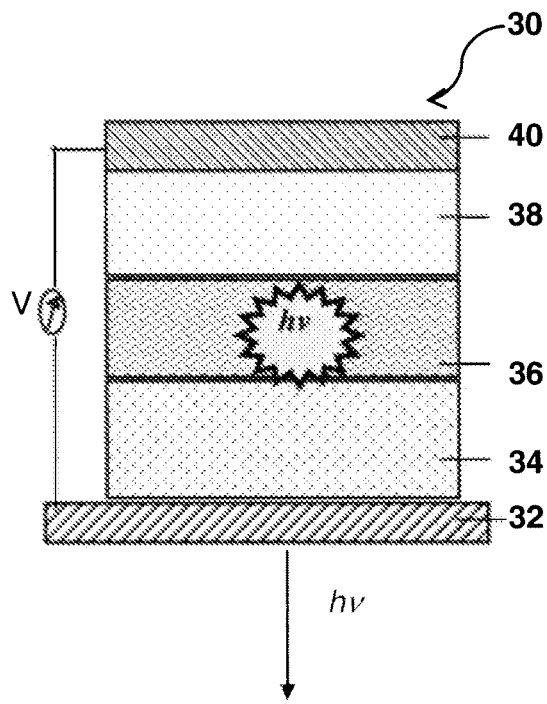
FIG. 3 illustrates a representative structure of an organic light-emitting device which can incorporate one or more compounds of the present teachings as electron-transporting and/or emissive and/or hole-transporting materials.

FIG. 3 illustrates a representative structure of an organic light-emitting diode (OLED) which can incorporate one or more compounds of the present teachings as electron-transporting and/or emissive and/or hole-transporting materials. As shown, an OLED generally includes a substrate 30 (not shown, e.g., glass), a transparent anode 32 (e.g., ITO), a cathode 40 (e.g., metal), and one or more organic layers which can incorporate one or more compounds of the present teachings as hole-transporting (n-channel) (layer 34 as shown) and/or emissive (layer 36 as shown) and/or electron-transporting (p-channel) materials (layer 38 as shown). In embodiments where the present compounds only have one or two of the properties of hole transport, electron transport, and emission, the present compounds can be blended with one or more further organic compounds having the remaining required property or properties.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-Vis spectra were recorded on a Cary Model 1 UV-vis spectrophotometer. NMR spectra were recorded on a Varian Unity Plus 500 spectrometer ($^1$H, 500 MHz; $^{13}$C, 125 MHz). Electrospray mass spectrometry was performed on a Thermo Finnegan model LCQ Advantage mass spectrometer.

Example 1

Synthesis of Compounds 2 and 3

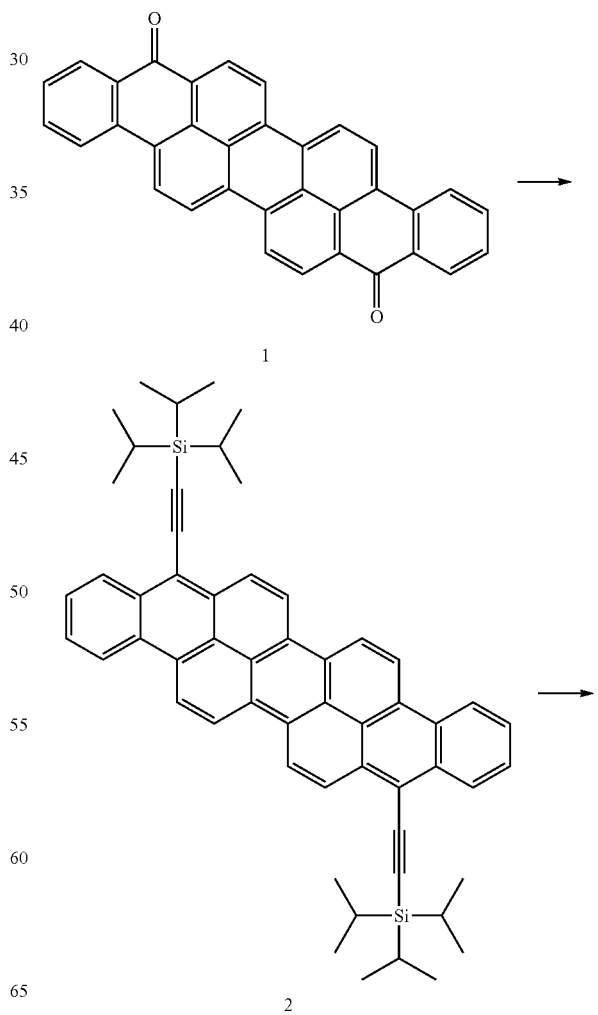

-continued

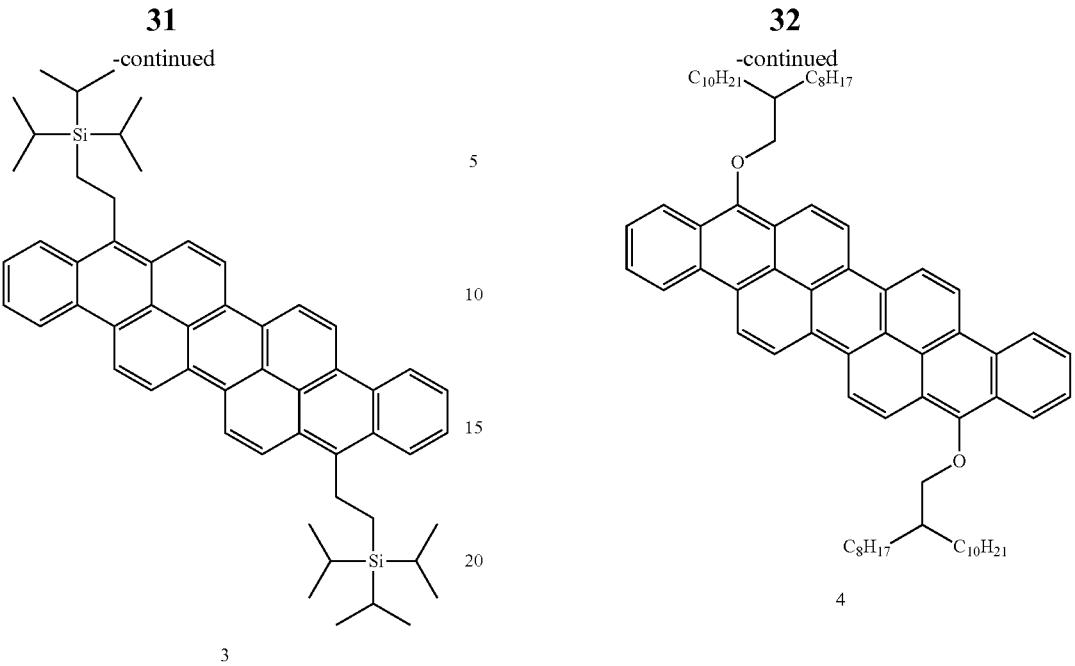

3

4

Figure 4:
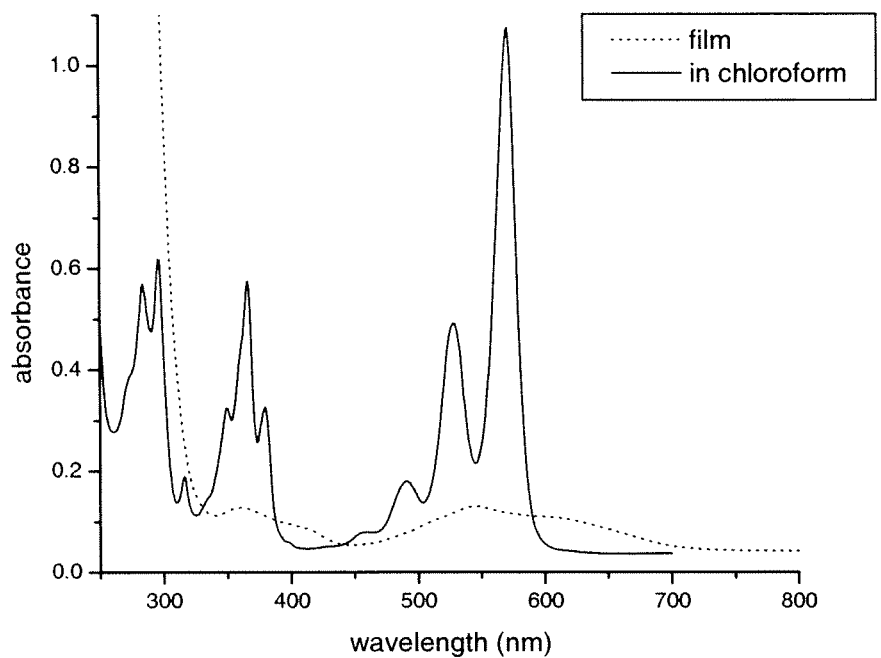
FIG. 4 shows the UV-vis spectra of compound 2 as a film and in chloroform.

A solution of 2.0 g (11.0 mmol) of triisopropylsilyl acetylene in 25 mL of tetrahydrofuran was cooled to 0° C. and treated with 4.0 mL (10.0 mmol) of n-BuLi (2.5 M in hexanes). The mixture was stirred at 60° C. for 30 min. then cooled to room temperature. The mixture was treated with 1.0 g (2.19 g) of isoviolanthrone (1, TCI America) and stirred at 60° C. for 2 h. The mixture was cooled to room temperature and treated with a solution of 2.0 g $SnCl_2$ in 4 mL of water and 1 mL of concentrated aqueous HCl. The mixture was stirred at 60° C. for 30 min., cooled to room temperature, treated with 50 mL of methanol, and filtered. The filter cake was washed with methanol until the washings were colorless. The dried solid was purified by flash chromatography (silica gel, toluene) and then recrystallized from chloroform to give 140 mg (8% yield) of dinaphthoperylene 2 as a crystalline purple solid. M.P.>400° C. Anal. calcd. for $C_{56}H_{58}Si_2$; C, 85.44; H, 7.43. found: C, 85.22; H, 7.31. FIG. 4 shows the UV-vis spectra of compound 2 as a film and in chloroform.

A mixture of 40 mg (0.0508 mmol) of compound 2 and 40 mg of 10% Pd/C in 150 mL of tetrahydrofuran under 1 atm $H_2$ was stirred for 20 h at room temperature. The mixture was passed through a short pad of silica gel and the filtrate was concentrated in vacuo to give compound 3 as a red solid.

Figure 5:
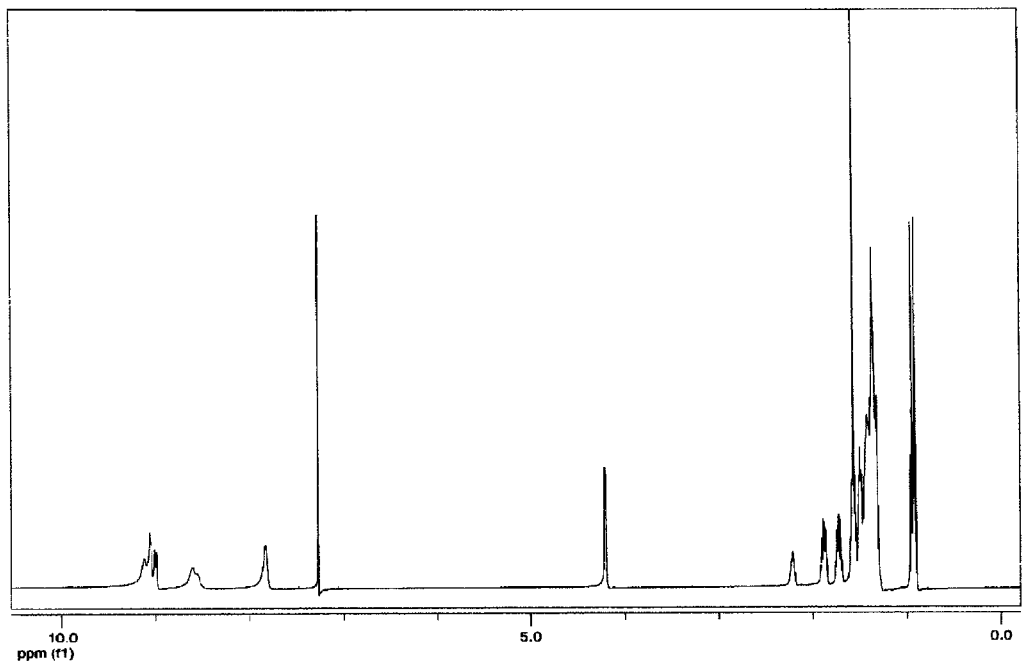
FIG. 5 shows the $^1$H NMR spectrum of compound 4 in $CDCl_3$.
Figure 6:
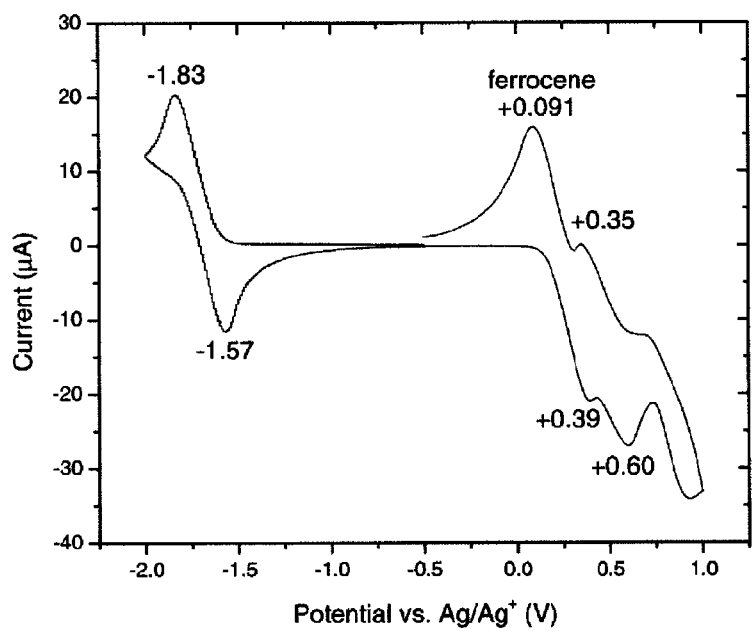
FIG. 6 shows a cyclic voltammetry plot of compound 4 with 0.1 M $Bu_4NPF_6$ in THF using Ag/Ag+ reference electrode and Pt working electrode.

A mixture of 0.25 g (0.548 mmol) of isoviolanthrone 1 and 0.25 g (1.44 mmol) of $Na_2S_2O_4$ was suspended in 25 mL of tetrahydrofuran under nitrogen and treated with 5 mL of 1.0 M aqueous NaOH. The mixture was stirred at room temperature with periodic sonication. When no visible solids remained (after about 1 h), the mixture was treated with 2.0 g (4.9 mmol) of 2-octyldodecyl iodide. The mixture was heated in an oil bath at 80° C. for 40 h. Tetrahydrofuran was removed in vacuo and the mixture was diluted with 50 mL of water. The mixture was extracted twice with 50 mL each of chloroform and the combined extracts were dried over $MgSO_4$, filtered, concentrated in vacuo, and purified by flash chromatography (silica gel, 4×25 cm, 1:1 toluene:hexanes). The concentrated product fraction was sonicated with methanol/acetone (3:1) and filtered. The filter cake was washed with methanol/acetone then with hexanes to give 0.35 g (63% yield) of dinaphthoperylene 4 as an orange solid. $^1$H NMR ($CDCl_3$): 9.2-7.8 (m, 16H), 4.19 (d, 4H, J=5.4 Hz), 2.20 (m, 2H), 1.87 (m, 4H), 1.70 (m, 4H), 1.60-1.25 (m, 56H), 0.95-0.87 (m, 12H). FIG. 5 shows the $^1$H NMR spectrum of compound 4 in $CDCl_3$. FIG. 6 shows a cyclic voltammetry plot of compound 4 with 0.1 M $Bu_4NPF_6$ in THF using Ag/Ag+ reference electrode and Pt working electrode.

Example 2

Synthesis of Compound 4

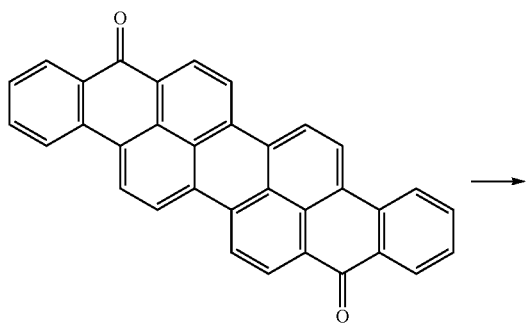

1

Example 3

Synthesis of Compound 6

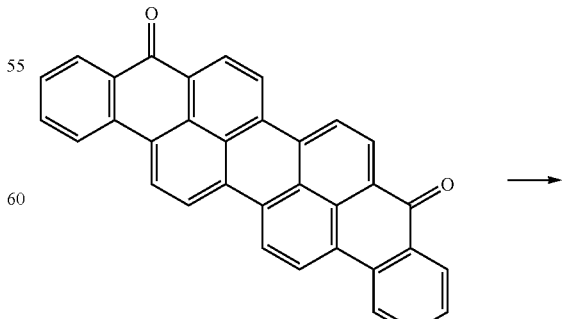

5

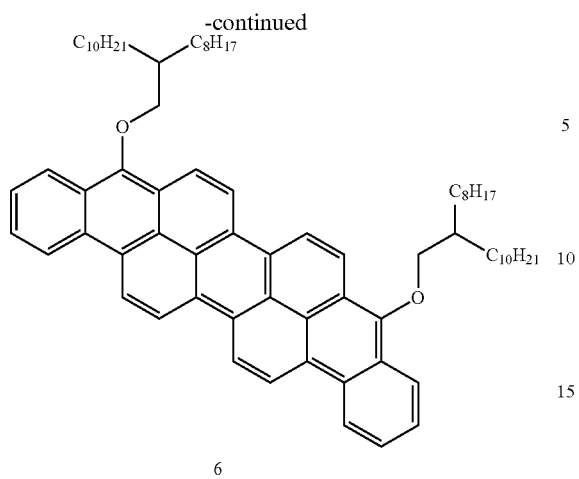

6

A mixture of 0.15 g (0.329 mmol) of violanthrone (5, Pfaltz & Bauer Chemicals) and 0.15 g (0.862 mmol) of Na$_2$S$_2$O$_4$ was suspended in 15 mL of tetrahydrofuran under nitrogen and treated with 3 mL of 1.0 M aqueous NaOH. The mixture was stirred at room temperature with periodic sonication. When no visible solids remained (after about 1 h), the mixture was treated with 1.2 g (2.9 mmol) 2-octyldodecyl iodide. The mixture was heated in an oil bath at 80° C. for 40 h. Tetrahydrofuran was removed in vacuo and the mixture was diluted with 50 mL of water. The mixture was extracted twice with 30 mL each of chloroform and the combined extracts were dried over MgSO$_4$, filtered, concentrated in vacuo, and purified by flash chromatography (silica gel, 4×25 cm, 1:2 toluene:hexanes) to give dinaphthoperylene 6 as a red oil.

Example 4

Synthesis of Compound 7

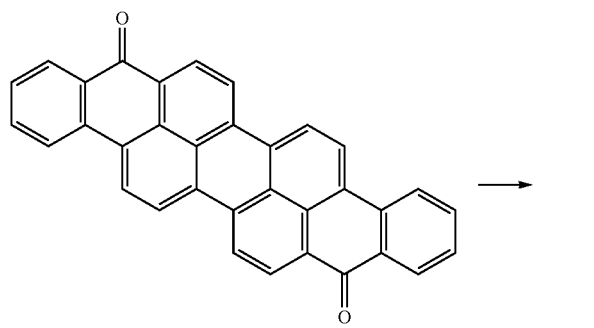

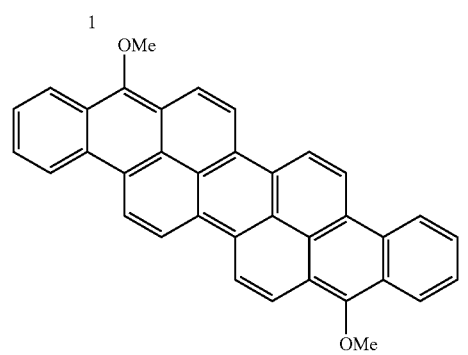

7

A mixture of 0.25 g (0.548 mmol) of isoviolanthrone 1 and 0.25 g (1.44 mmol) of Na$_2$S$_2$O$_4$ was suspended in 25 mL of tetrahydrofuran under nitrogen and treated with 5 mL of 1.0 M aqueous NaOH. The mixture was stirred at room temperature with periodic sonication. When no visible solids remained (after about 1 h), the mixture was treated with 10 mL (105 mmol) of dimethyl sulfate. The mixture was stirred at room temperature for 30 min. The precipitate was filtered off and washed successively with water and THF and dried to give 0.16 g (60% yield) of compound 7 as a brown solid.

Example 5

Synthesis of Compound 8

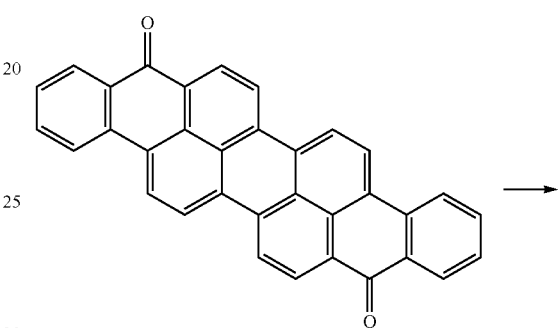

1

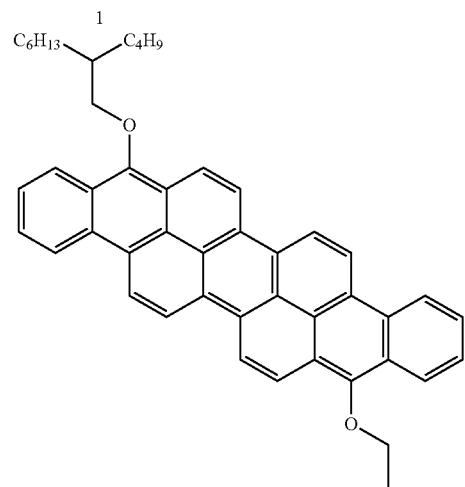

8

A mixture of 0.30 g (0.657 mmol) of isoviolanthrone 1 and 0.30 g (1.72 mmol) of Na$_2$S$_2$O$_4$ was suspended in 30 mL of tetrahydrofuran under nitrogen and treated with 6 mL of 1.0 M aqueous NaOH. The mixture was stirred at room temperature with periodic sonication. When no visible solids remained (after about 1 h), the mixture was treated with 2.0 g (6.75 mmol) of 2-butyloctyl iodide. The mixture was heated in an oil bath at 80° C. for 43 h. Tetrahydrofuran was removed in vacuo and the mixture was extracted with 100 mL of methylene chloride. The separated organic layer was dried over MgSO$_4$, filtered, concentrated in vacuo, and purified by flash chromatography (silica gel, 4×25 cm, 1:1 toluene:hexanes). The concentrated product fraction was sonicated with acetone and filtered. The filter cake was washed with acetone then with hexanes to give 0.31 g (59% yield) of compound 8 as a brown solid. $^1$H NMR (CDCl$_3$): 9.2-7.8 (m, 16H), 4.2 (m, 4H), 2.2-0.9 (m, 46H).

Example 6

Synthesis of Compound 9

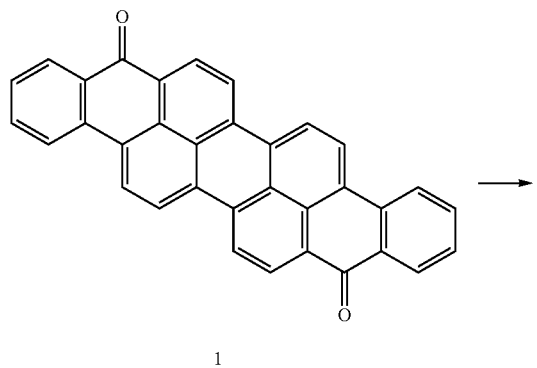

A mixture of 0.35 g (0.767 mmol) of isoviolanthrone 1 and 0.35 g (2.01 mmol) of Na$_2$S$_2$O$_4$ was suspended in 35 mL of tetrahydrofuran under nitrogen and treated with 7 mL of 1.0 M aqueous NaOH. The mixture was stirred at room temperature with periodic sonication. When no visible solids remained (after about 1 h), the mixture was treated with 1.9 g (4.16 mmol) of 2-ethylhexyl iodide. The mixture was heated in an oil bath at 80° C. for 40 h. The mixture was cooled to room temperature, treated with 100 mL of methanol, and filtered. The filter cake was purified by flash chromatography (silica gel, 4×25 cm, chloroform). The concentrated product fraction was sonicated with acetone and filtered. The filter cake was washed with acetone then with hexanes to give 0.25 g (48% yield) of compound 9 as a brown solid. $^1$H NMR (CDCl$_3$): 9.2-7.8 (m, 16H), 4.2 (m, 4H), 2.2-0.9 (m, 30H).

Example 7

Device Fabrication

Figure 7:
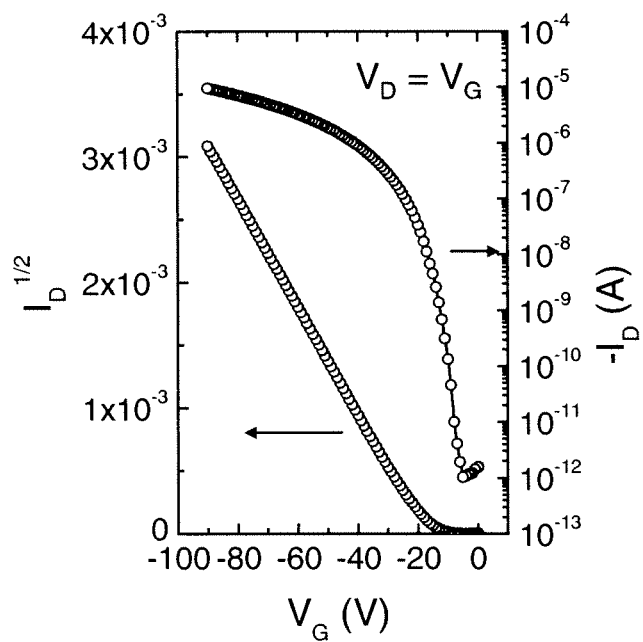
FIG. 7 shows a representative transfer plot (current vs. gate voltage) of compound 2 in a bottom-gate top-contact device.

Bottom-gate top contact TFTs were fabricated using compounds of the present teachings as the semiconductor layer. N-doped silicon wafers (100) with 3000 Å thermally grown silicon dioxide layer (Addison Inc.) were used as device substrates. Prior to the semiconductor deposition, the Si/SiO$_2$ surfaces were modified through an octadecyltrichlorosilane (OTS) treatment process. Thin films of approximately 40-120 nm in thickness were prepared through physical vapor deposition, with the deposition rate of 0.1-0.5 Å/s and the substrate temperature of 30-120° C. The TFTs were completed by vapor deposition of 300 Å gold source/drain electrodes onto the semiconductor layer through a stencil mask to define the transistor channel. The channel lengths and widths were 50-200 μm and 500-2000 μm, respectively. The gate electrode was accessed through an ohmic contact to the doped silicon. Mobility of 0.01~0.03 cm$^2$/Vs was obtained for compound 2, with threshold voltage of −10~1−30 V, and on-off current ratio of 10$^5$~10$^7$. A representative transfer plot (current vs. gate voltage) of a bottom-gate top contact device incorporating compound 2 is shown in FIG. 7.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound having formula IA or IB:

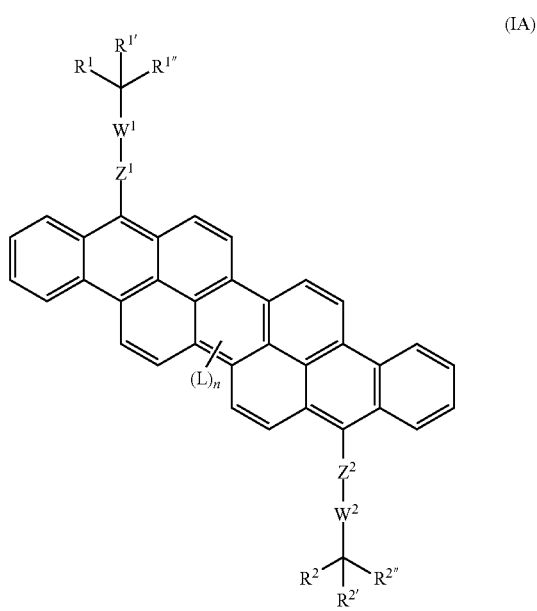

(IA)

(IB)

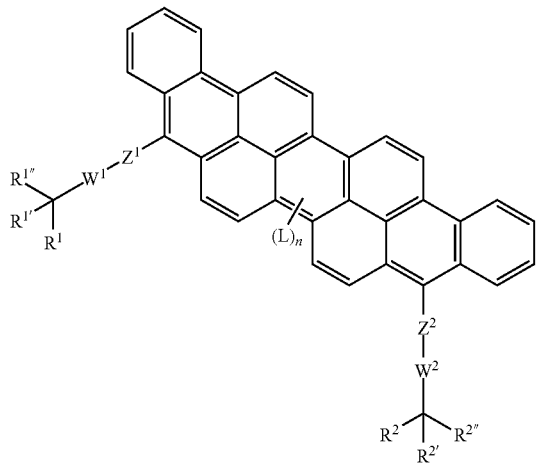

wherein:

$W^1$ and $W^2$ independently are $-(CR^aR^b)_m$;

$Z^1$ and $Z^2$ independently are selected from the group consisting of O, S, and a covalent bond;

L, at each occurrence, independently is an electron-withdrawing group;

$R^a$ and $R^b$, at each occurrence, independently are selected from the group consisting of H, a $C_{1-20}$ alkyl group, and a $C_{1-20}$ haloalkyl group;

$R^1$, $R^{1'}$, $R^{1''}$, $R^2$, $R^{2'}$, and $R^{2''}$ independently are selected from the group consisting of H, a $C_{1-20}$ alkyl group, a $C_{2-20}$ alkenyl group, and a $C_{1-20}$ haloalkyl group, wherein at least two of $R^1$, $R^{1'}$, and $R^{1''}$ and at least two of $R^2$, $R^{2'}$, and $R^{2''}$ are selected from a $C_{1-20}$ alkyl group, a $C_{2-20}$ alkenyl group, and a $C_{1-20}$ haloalkyl group;

m, at each occurrence, independently is 0, 1, 2, 3, 4, 5, 6, 7, 8, 9, or 10; and n is 0, 1, 2, 3, 4, 5, 6, 7 or 8.

2. The compound of claim 1, wherein the compound has formula IIA or IIB:

(IIA)

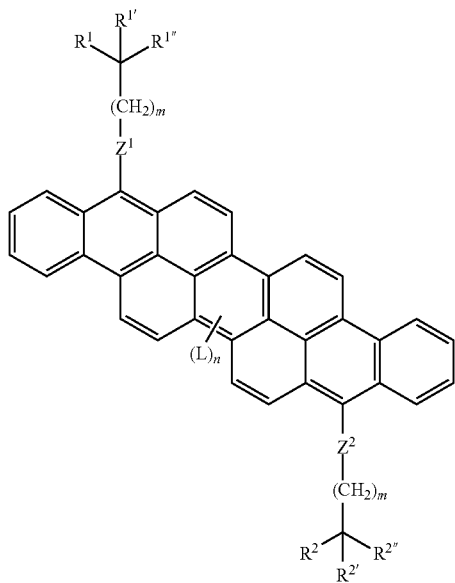

(IIB)

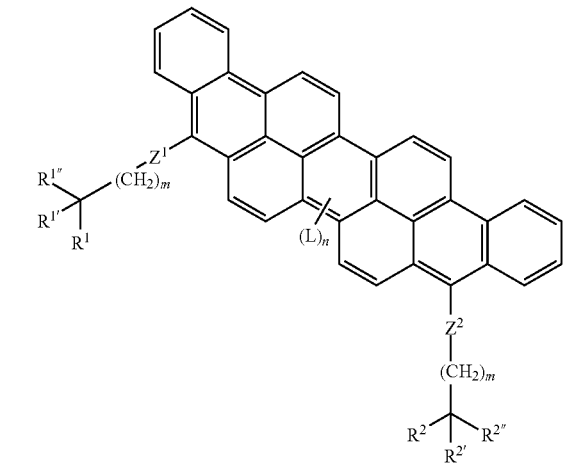

wherein L, $R^1$, $R^{1'}$, $R^{1''}$, $R^2$, $R^{2'}$, $R^{2''}$, $Z^1$, $Z^2$, m and n are as defined in claim 1.

3. The compound of claim 1, wherein the compound has formula IIIA or IIIB:

(IIIA)

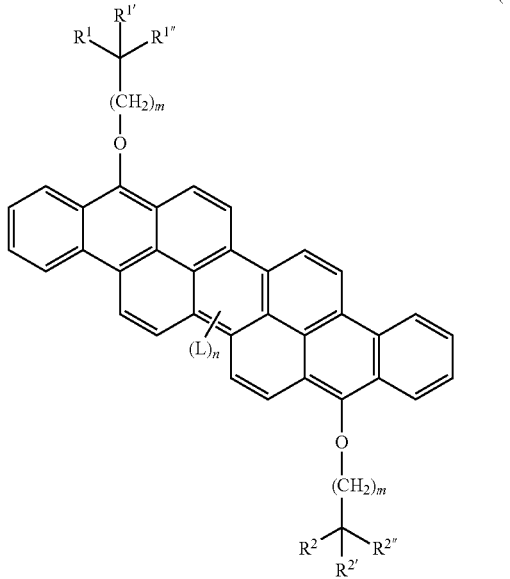

(IIIB)

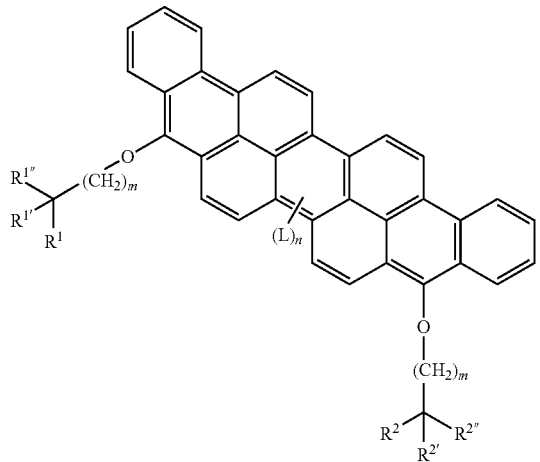

wherein L, $R^1$, $R^{1'}$, $R^{1''}$, $R^2$, $R^{2'}$, $R^{2''}$, m and n are as defined in claim 1.

4. The compound of claim 1, wherein the compound has formula VA or VB:

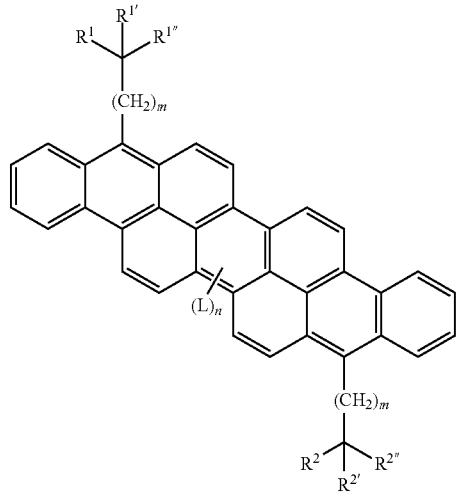

(VA)

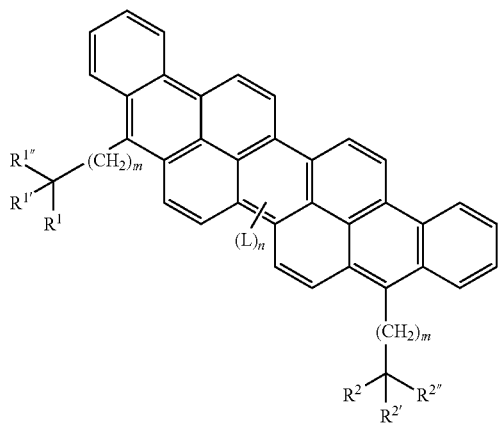

(VB)

wherein L, $R^1$, $R^{1'}$, $R^{1''}$, $R^2$, $R^{2'}$, $R^{2''}$, m and n are as defined in claim 1.

5. The compound of claim 1, wherein each m independently is 1 or 2.

6. The compound of claim 5, wherein $R^1$, $R^{1'}$, $R^2$, and $R^{2'}$ independently are selected from the group consisting of a linear $C_{1-20}$ alkyl group, a linear $C_{2-20}$ alkenyl group, and a linear $C_{1-20}$ haloalkyl group; and $R^{1''}$ and $R^{2''}$ are H.

7. The compound of claim 6, wherein L, at each occurrence, independently is selected from the group consisting of Br, CN, and $NO_2$; and n is 1, 2, 3, 4, 5, 6, 7 or 8.

8. The compound of claim 1, wherein the compound has formula IIAa:

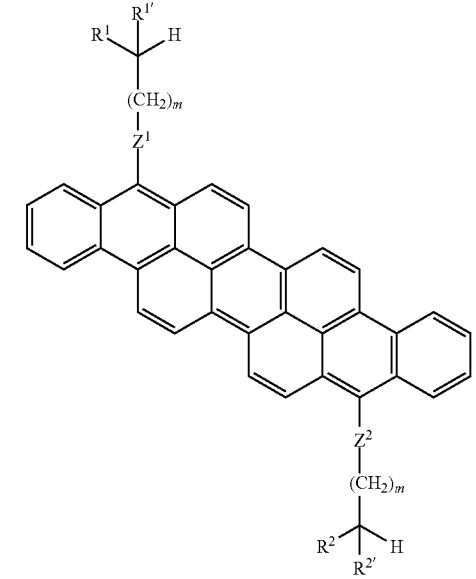

(IIAa)

wherein $R^1$ and $R^2$ independently are selected from the group consisting of a linear $C_{3-20}$ alkyl group, a linear $C_{4-20}$ alkenyl group, and a linear $C_{3-20}$ haloalkyl group; $R^{1'}$ and $R^{2'}$ independently are selected from the group consisting of $CH_3$, $CF_3$, $C_2H_5$, $CH_2CF_3$, $CF_2CH_3$, and $C_2F_5$; and $Z^1$, $Z^2$, and m are as defined in claim 1.

9. The compound of claim 8, wherein the compound has formula IIAb or IIAc:

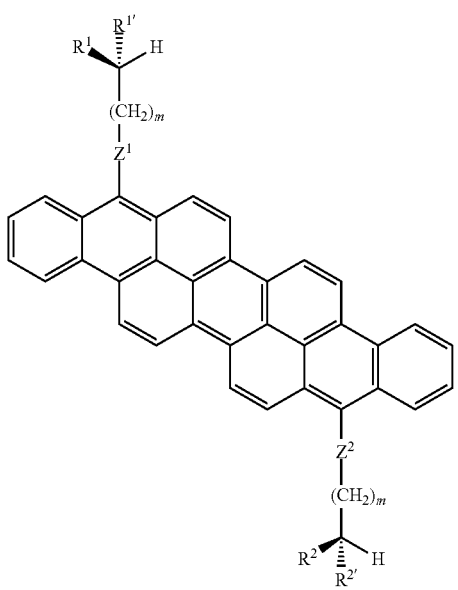

(IIAb)

(IIAc)

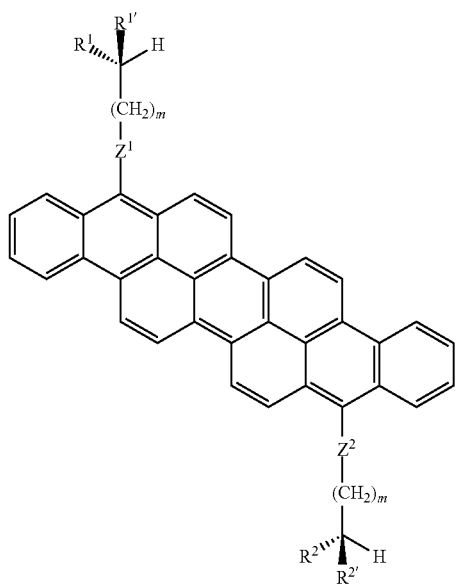

wherein $R^1$, $R^{1'}$, $R^2$, $R^{2'}$, $Z^1$, $Z^2$, and m are as defined in claim 8.

10. The compound of claim 1, wherein the compound has formula IIIAa or VAa:

(VAa)

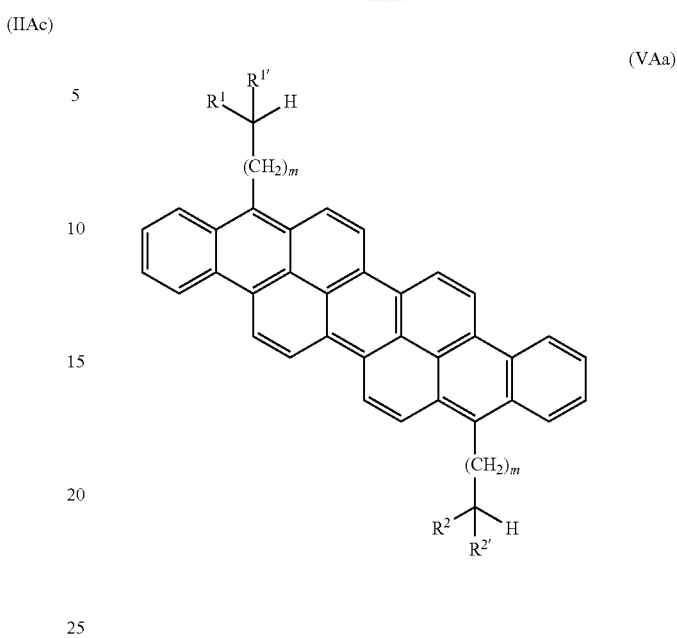

wherein $R^1$ and $R^2$ independently are selected from the group consisting of a linear $C_{3-20}$ alkyl group, a linear $C_{4-20}$ alkenyl group, and a linear $C_{3-20}$ haloalkyl group; $R^{1'}$ and $R^{2'}$ independently are selected from $CH_3$, $CF_3$, $C_2H_5$, $CH_2CF_3$, $CF_2CH_3$, and $C_2F_5$; and each m independently is selected from 0, 1, and 2.

11. The compound of claim 10, wherein the compound has formula IIIAb, IIIAc, VAb, or VAc:

(IIIAa)

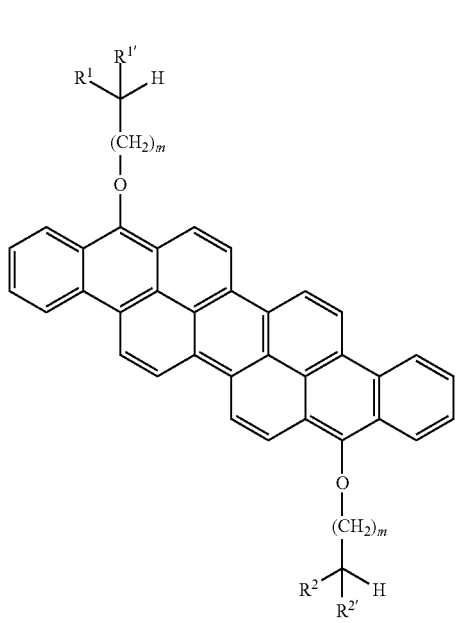

(IIIAb)

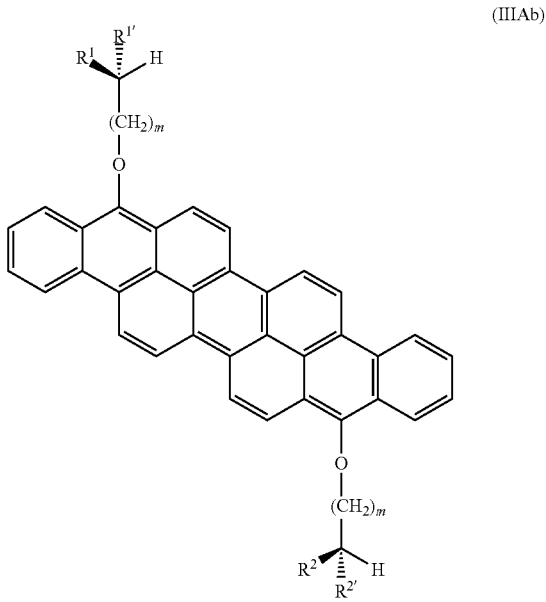

-continued (IIIAc)

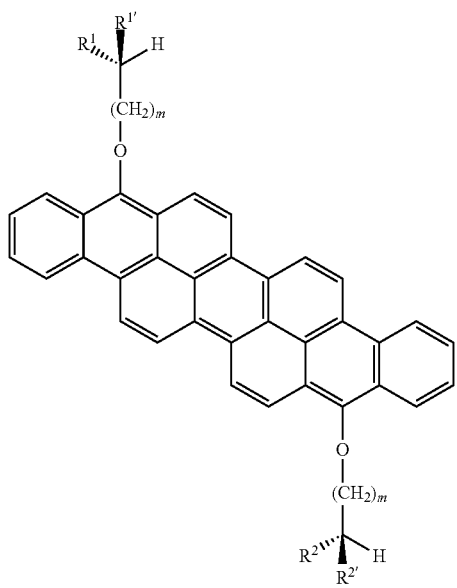

(VAb)

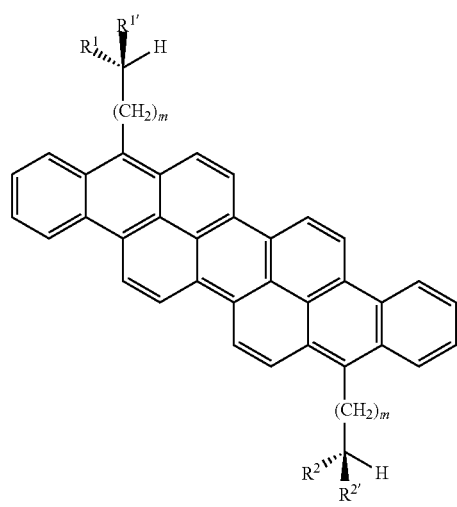

(VAc)

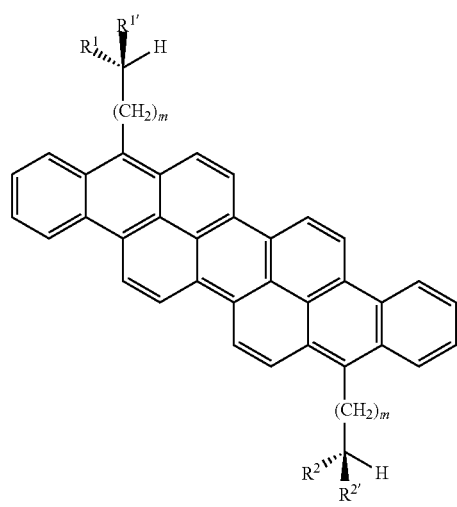

wherein R¹, R¹', R², R²', and m are as defined in claim 10.

12. A thin film semiconductor comprising a compound of claim 1.

13. A composite comprising a substrate and the thin film semiconductor of claim 12 deposited on the substrate.

14. An electronic device, an optical device, or an optoelectronic device comprising the thin film semiconductor of claim 12.

15. A field effect transistor device comprising a source electrode, a drain electrode, a gate electrode, and the thin film semiconductor of claim 12 in contact with a dielectric material, wherein the dielectric material comprises an organic dielectric material, an inorganic dielectric material, or a hybrid organic/inorganic dielectric material.

16. The field effect transistor device of claim 15, wherein the field effect transistor has a structure selected from top-gate bottom-contact structure, bottom-gate top-contact structure, top-gate top-contact structure, and bottom-gate bottom-contact structure.

17. The compound of claim 1, wherein the compound is

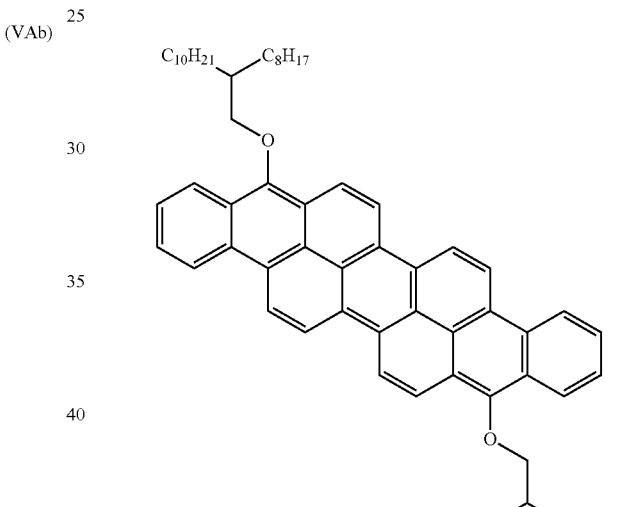

18. The compound of claim 1, wherein the compound is

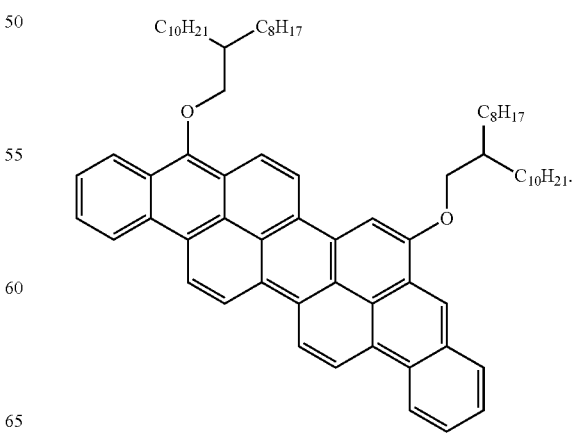

19. The compound of claim 1, wherein the compound is
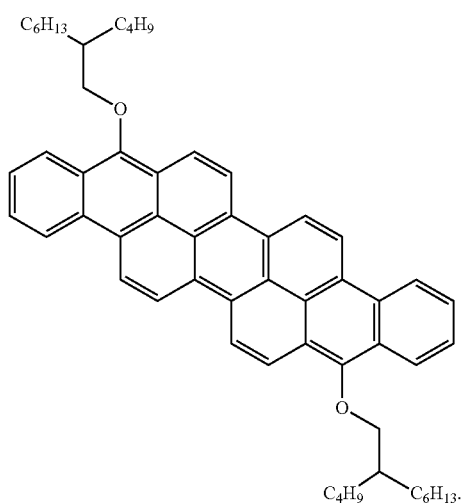
20. The compound of claim 1, wherein the compound is
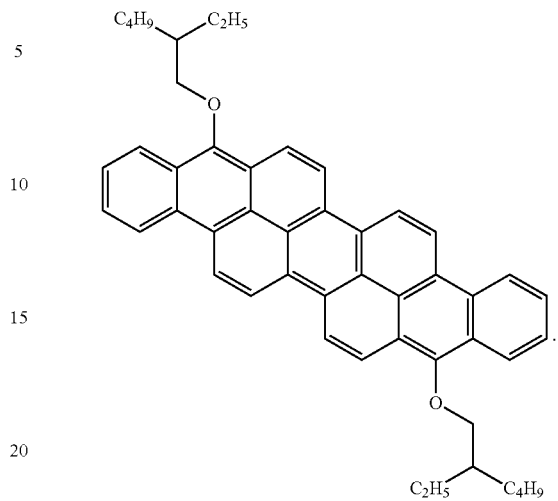
* * * * *